(12) United States Patent
Ho et al.

(10) Patent No.: US 12,180,296 B2
(45) Date of Patent: Dec. 31, 2024

(54) CROSS SPECIES SINGLE DOMAIN ANTIBODIES TARGETING MESOTHELIN FOR TREATING SOLID TUMORS

(71) Applicant: The U.S.A., as represented by the Secretary, Department of Health and Human Services, Bethesda, MD (US)

(72) Inventors: Mitchell Ho, Urbana, MD (US); Ira H. Pastan, Potomac, MD (US); Jessica D. Hong, Herndon, VA (US); Nan Li, Laurel, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 847 days.

(21) Appl. No.: 17/421,334

(22) PCT Filed: Jan. 2, 2020

(86) PCT No.: PCT/US2020/012021
§ 371 (c)(1),
(2) Date: Jul. 7, 2021

(87) PCT Pub. No.: WO2020/146182
PCT Pub. Date: Jul. 16, 2020

(65) Prior Publication Data
US 2022/0064324 A1    Mar. 3, 2022

Related U.S. Application Data

(60) Provisional application No. 62/789,650, filed on Jan. 8, 2019.

(51) Int. Cl.
| | | |
|---|---|---|
| C07K 16/30 | (2006.01) | |
| A61K 39/00 | (2006.01) | |
| A61K 47/68 | (2017.01) | |
| A61K 47/69 | (2017.01) | |
| A61P 35/00 | (2006.01) | |
| C07K 14/705 | (2006.01) | |
| C07K 14/71 | (2006.01) | |
| C07K 14/715 | (2006.01) | |
| C07K 14/725 | (2006.01) | |
| C07K 16/28 | (2006.01) | |
| A61K 38/00 | (2006.01) | |

(52) U.S. Cl.
CPC .......... *C07K 16/30* (2013.01); *A61K 39/4611* (2023.05); *A61K 39/4631* (2023.05); *A61K 39/464468* (2023.05); *A61K 47/6851* (2017.08); *A61K 47/6929* (2017.08); *A61P 35/00* (2018.01); *C07K 14/7051* (2013.01); *C07K 14/70517* (2013.01); *C07K 14/70578* (2013.01); *C07K 14/71* (2013.01); *C07K 14/7153* (2013.01); *C07K 16/2809* (2013.01); *A61K 38/00* (2013.01); *A61K 2039/505* (2013.01); *A61K 2239/31* (2023.05); *A61K 2239/38* (2023.05); *A61K 2239/55* (2023.05); *C07K 2317/22* (2013.01); *C07K 2317/31* (2013.01); *C07K 2317/565* (2013.01); *C07K 2317/569* (2013.01); *C07K 2319/02* (2013.01); *C07K 2319/03* (2013.01); *C07K 2319/30* (2013.01); *C07K 2319/33* (2013.01)

(58) Field of Classification Search
None
See application file for complete search history.

(56) References Cited

U.S. PATENT DOCUMENTS

2018/0326060 A1    11/2018    Wesche et al.

FOREIGN PATENT DOCUMENTS

| CN | 101012280 A | 8/2007 | |
|---|---|---|---|
| CN | 108129566 | 6/2018 | |
| WO | WO 2014/052064 | 4/2014 | |
| WO | WO 2016/126608 | 8/2016 | |
| WO | WO-2021119539 A1 * | 6/2021 | ............. A61K 35/15 |

OTHER PUBLICATIONS

International Search Report and Written Opinion for PCT/US2020/012021, mailed on Apr. 3, 2020 (12 pages).
Montemagno et al., "Preclinical Evaluation of Mesothelin-Specific Ligands for SPECT Imaging of Triple-Negative Breast Implant," *J. Nucl. Med.*, vol. 59:1056-1062, 2018.
Nagaya et al., "Near Infrared Photoimmunotherapy with an Anti-Mesothelin Antibody," *Oncotarget*, vol. 7:23361-23369, 2016.
Tang et al., "A Human Single-Domain Antibody Elicits Potent Antitumor Activity by Targeting an Epitope in Mesothelin Close to the Cancer Cell Surface," *Mol. Cancer Ther.*, vol. 12:416-426, 2013.

* cited by examiner

*Primary Examiner* — Amy E Juedes
*Assistant Examiner* — James Ryland Melchior
(74) *Attorney, Agent, or Firm* — Klarquist Sparkman, LLP

(57) ABSTRACT

Camel single-domain monoclonal antibodies that specifically bind human and mouse mesothelin are described. Chimeric antigen receptor (CAR) T cells and antibody conjugates based on the mesothelin-specific antibodies are also described. The disclosed CAR T cells, mesothelin-specific antibodies and conjugates thereof can be used, for example, in the diagnosis or treatment of mesothelin-positive cancers.

40 Claims, 22 Drawing Sheets
Specification includes a Sequence Listing.

Human mesothelioma M30

Human mesothelioma H226

Human ovarian cancer OVCAR8

Human pancreatic cancer Panc3.014

Human pancreatic cancer
KLM1

Human pancreatic cancer
T3M4

Human cholangiocarcinoma
KMBC

Human cholangiocarcinoma
OZ

Mouse pancreatic cancer
PDA95775

Mouse pancreatic cancer
CREP133234

Mouse pancreatic cancer
CREP133239

Human mesothelioma
M30

Human mesothelioma
H226

Human ovarian cancer
OVCAR8

Human pancreatic cancer
Panc3.014

Human pancreatic cancer
KLM1

Human pancreatic cancer
T3M4

Human cholangiocarcinoma
KMBC

Human cholangiocarcinoma
OZ

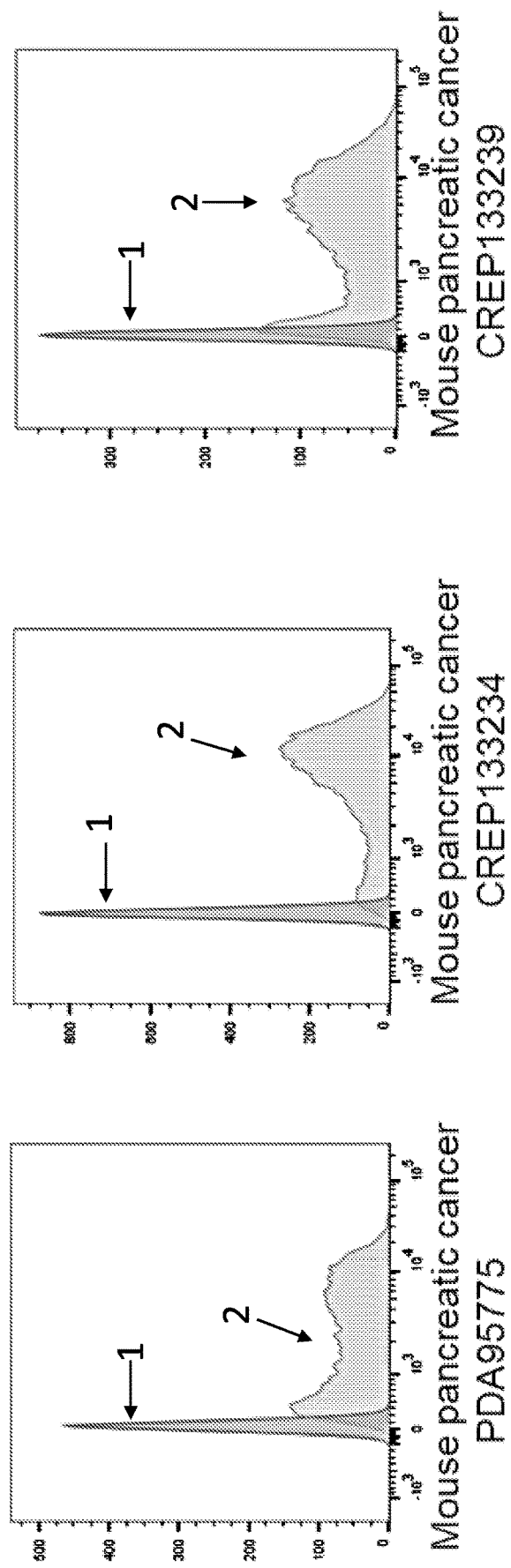

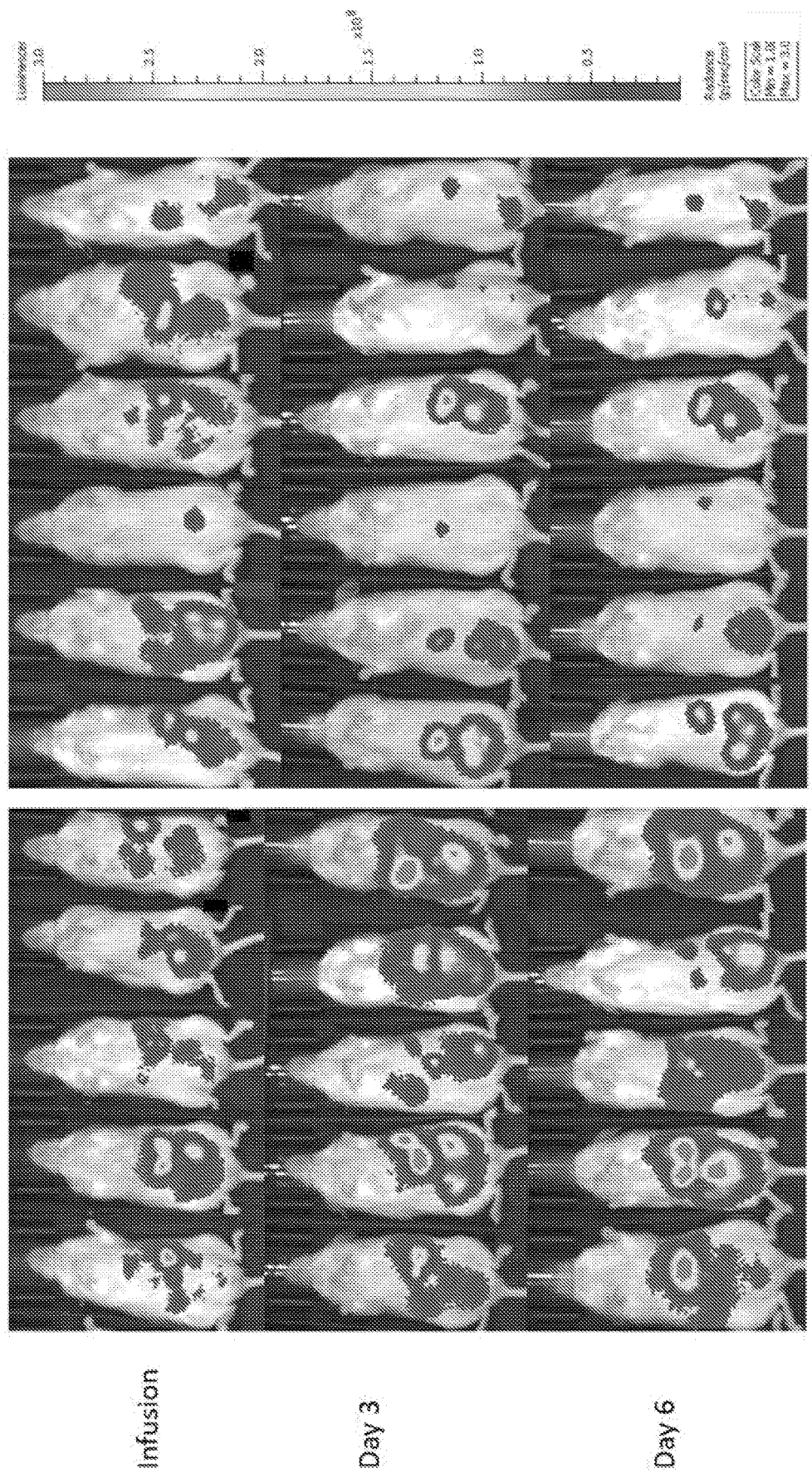

CROSS SPECIES SINGLE DOMAIN ANTIBODIES TARGETING MESOTHELIN FOR TREATING SOLID TUMORS

CROSS REFERENCE TO RELATED APPLICATIONS

This application is the U.S. National Stage of International Application No. PCT/US2020/012021, file Jan. 2, 2020, which was published in English under PCT Article 21(2), which claims the benefit of U.S. Provisional Application No. 62/789,650, filed Jan. 8, 2019, which are herein incorporated by reference in their entirety.

ACKNOWLEDGMENT OF GOVERNMENT SUPPORT

This invention was made with government support under project number Z01 BC010891 awarded by the National Institutes of Health. The government has certain rights in the invention.

FIELD

This disclosure concerns camel single-domain monoclonal antibodies that specifically bind both human and mouse mesothelin. This disclosure further concerns use of the mesothelin-specific antibodies, such as in immunotherapy for the treatment of mesothelin-expressing tumors.

BACKGROUND

The mesothelin (MSLN) gene encodes a ~70 kDa precursor protein that is processed to a ~30 kDa N-terminal protein and a ~40 kDa C-terminal membrane-bound mature mesothelin (Hassan and Ho, *Eur J Cancer* 44:46-53, 2008). Mesothelin is present at relatively low levels in mesothelial cells of the pleura, peritoneum and pericardium of healthy individuals, but is highly expressed in malignant mesotheliomas (Chang et al., *Cancer Res* 52:181-186, 1992; Chang and Pastan, *Proc Natl Acad Sci USA* 93:136-140, 1996) and other solid tumors, such as stomach cancer, squamous cell carcinomas, prostate cancer, pancreatic cancer, lung cancer, cholangiocarcinoma, breast cancer and ovarian cancer (Hassan et al., *Clin. Cancer Res.* 10:3937-3942, 2004; McGuire et al., *N. Engl. J. Med.* 334:1-6, 1996; Argani et al., *Clin. Cancer Res.* 7:3862-3868, 2001; Hassan et al., *Appl. Immunohistochem. Mol. Morphol.* 13:243-247, 2005; Li et al., *Mol. Cancer Ther.* 7:286-296, 2008; Yu et al., *J Cancer* 1:141-1749, 2010; Tchou et al., *Breast Cancer Res Treat* 133(2):799-804, 2012; U.S. Pat. No. 7,081,518).

Mesothelin is a well-established tumor target in multiple solid tumors. Although a number of mesothelin-specific antibodies and CAR-expressing T cells have been developed and many clinical trials to evaluate these antibodies and CAR T cells targeting mesothelin are ongoing, no antibodies have been reported to be cross species, in particular with high binding affinity for both human and mouse mesothelin-positive cells. Furthermore, no CAR T cells targeting mesothelin have been shown to have potent anti-tumor activity in mice and humans. Thus, there remains a need for mesothelin-specific antibodies that bind both mouse and human mesothelin to enable evaluation of the safety and efficacy of therapeutic antibodies in animal models.

SUMMARY

The present disclosure describes two cross species mesothelin-specific camel single-domain monoclonal antibodies isolated by phage display. The mesothelin-specific antibodies, referred to as A101 and G8, specifically bind both human and mouse mesothelin with high affinity. Chimeric antigen receptor (CAR) T cells comprised of the disclosed antibodies are capable of potently killing mesothelin-positive tumor cells in vitro and in vivo.

Provided herein are single-domain monoclonal antibodies that bind, such as specifically bind, mesothelin. In some embodiments, the monoclonal antibody or includes the complementarity determining region (CDR) sequences of A101 or G8. Also provided herein are conjugates that include a disclosed monoclonal antibody. In some examples, provided are CARs (and CAR-expressing T cells and natural killer cells), immunoconjugates (such as immunotoxins), multi-specific antibodies, antibody-drug conjugates (ADCs), antibody-nanoparticles, conjugates or fusion proteins that include a monoclonal antibody disclosed herein. Compositions that include a mesothelin-specific monoclonal antibody and a pharmaceutically acceptable carrier are also provided by the present disclosure.

Also provided herein are nucleic acid molecules and vectors encoding the mesothelin-specific monoclonal antibodies, CARs, immunoconjugates (such as immunotoxins), multi-specific antibodies and fusion proteins disclosed herein.

Further provided are nucleic acid constructs that encode both a mesothelin-specific CAR and a truncated human epidermal growth factor receptor (huEGFRt). The encoded CARs include a mesothelin-specific single-domain monoclonal antibody fused to an extracellular hinge region, a transmembrane region, an intracellular co-stimulatory domain and an intracellular signaling domain. The huEGFRt includes two EGFR extracellular domains (Domain III and Domain IV) and the EGFR transmembrane domain, but lacks the two membrane distal extracellular domains and all intracellular domains. In some embodiments, the nucleic acid molecule includes, in the 5' to 3' direction, a nucleic acid encoding a first signal sequence; a nucleic acid encoding a mesothelin-specific antibody; a nucleic acid encoding an extracellular hinge region; a nucleic acid encoding a transmembrane domain; a nucleic acid encoding an intracellular co-stimulatory domain; a nucleic acid encoding a intracellular signaling domain; a nucleic acid encoding a self-cleaving 2A peptide; a nucleic acid encoding a second signal sequence; and a nucleic acid encoding a huEGFRt. Also provided are vectors, such as viral vectors, that include a nucleic acid molecule disclosed herein. Isolated cells, such as T lymphocytes, that co-express the disclosed CARs and huEGFRt are also disclosed.

Methods of treating a mesothelin-positive cancer in a subject, and methods of inhibiting tumor growth or metastasis of a mesothelin-positive cancer in a subject are also provided. In some embodiments, the methods include administering to the subject a monoclonal antibody disclosed herein, or administering to the subject a CAR (or CAR T cells or CAR NK cells), immunoconjugate (such as an immunotoxin), ADC, multi-specific antibody, antibody-nanoparticle conjugate or fusion protein comprising a monoclonal antibody disclosed herein.

Further provided herein are methods of detecting expression of mesothelin in a sample. In some embodiments, the method includes contacting the sample with a monoclonal antibody disclosed herein, and detecting binding of the antibody to the sample.

Also provided are methods of diagnosing a subject as having a mesothelin-positive cancer. In some embodiments, the method includes contacting a sample obtained from the subject with a monoclonal antibody disclosed herein, and detecting binding of the antibody to the sample.

The foregoing and other objects and features of the disclosure will become more apparent from the following detailed description, which proceeds with reference to the accompanying figures.

BRIEF DESCRIPTION OF THE DRAWINGS

(FIG. 5A) M30 and H226 are human mesothelioma cancer cells; OVCAR8 is a human ovarian cancer cell line; and Panc3.014 is a human pancreatic cancer cell line. (FIG. 5B) KLM1 and T3M4 are human pancreatic cancer cell lines; and KMBC and OZ are human cholangiocarcinoma cancer cell lines. (FIG. 5C) PDA95775, CREP133234, and CREP133239 are mouse pancreatic cancer cell lines. Peaks labelled "1" represent cell surface staining with isotype control, and peaks labelled "2" represent cell surface staining of mesothelin. A101 at 10 µg/ml was used for staining.

FIGS. 6A-6C: Flow cytometry analysis of cell surface mesothelin expression using the G8 antibody. (FIG. 6A) M30 and H226 are human mesothelioma cancer cells; OVCAR8 is a human ovarian cancer cell line; and Panc3.014 is a human pancreatic cancer cell line. (FIG. 6B) KLM1, and T3M4 are human pancreatic cancer cell lines; and KMBC and OZ are human cholangiocarcinoma cancer cell lines. (FIG. 6C) PDA95775, CREP133234, and CREP133239 are mouse pancreatic cancer cell lines. Peaks labelled "1" represent cell surface staining with isotype control, and peaks labelled "2" represent cell surface staining of mesothelin. G8 at 10 µg/ml was used for staining.

(FIG. 7A) Schematic diagram of the lentiviral construct expressing CARs targeting mesothelin along with truncated human EGFR (huEGFRt) using the T2A ribosomal skipping sequence. (FIG. 7B) Expression of mesothelin-targeted CARs on human T cells transduced with lentiviral particles was analyzed using flow cytometry detection of huEGFRt expression.

(FIG. 9A) Experimental schematic. H226 tumor-bearing NSG mice were treated with either peritoneal injection of mock T cells or 20×10$^6$ CAR T cells at day 13 after tumor cell inoculation. Tumor burden were monitored by bioluminescent imaging. (FIG. 9B) A101 CAR T cells demonstrated antitumor activity and showed a trend toward eradication of H226 xenograft tumors. (FIG. 9C) Quantitation of bioluminescence in mice treated in FIG. 8B.

(FIG. 10A) Production of human mesothelin fragments, including the constructs encoding amino acid residues 296-390 (Region I), 391-486 (Region II), and 487-581 (Region III) of mesothelin, as well as the constructs encoding smaller fragments within Region I: Region IAB (296-359), Region IBC (328-405), Region IA (296-337), Region IB (328-369), and Region IC (360-405). Region IAB (269-359) mutants having either E321A, W321A or Y318A substitutions were also generated. (FIG. 10B) The A101 and G8 camel single domain antibodies primarily bind to the N-terminal Region I (296-390) of mesothelin, including the IAB domain (64 residues, 296-359), as determined by ELISA. When tyrosine residue 318 was mutated to alanine (Y318A), A101 and G8 binding was lost.

(FIG. 13A) Transduction efficiency of CAR T cells expressing A101 and G8 antibodies. PBMCs from healthy donors were transduced with the A101 or G8 camel VHH. Cetuximab was used to detect CARs on the cell surface. (FIG. 13B) CAR T cell killing assay. Both A101 and G8 CAR T cells kill mesothelin-positive lines (H9, KLM1 and H226), but not mesothelin-negative cells (A431).

FIGS. 14A-14B: Testing of A101 CAR T cells in mice bearing peritoneal human mesothelioma xenografts. Seven-week old female NSG mice were inoculated with 2M H226-luc cells. At day 3, animals were treated with either Mock T cells or A101 CAR T cells. (FIG. 14A) Bioluminescence images of mock-treated and A101-treated mice. (FIG. 14B) Schematic of the study (top) and a graph showing radiance of mock-treated and A101-treated animals (bottom) as a measure of tumor size. The A101 CAR effectively inhibited the growth of H226 xenograft tumors in mice.

SEQUENCE LISTING

Figure 1:
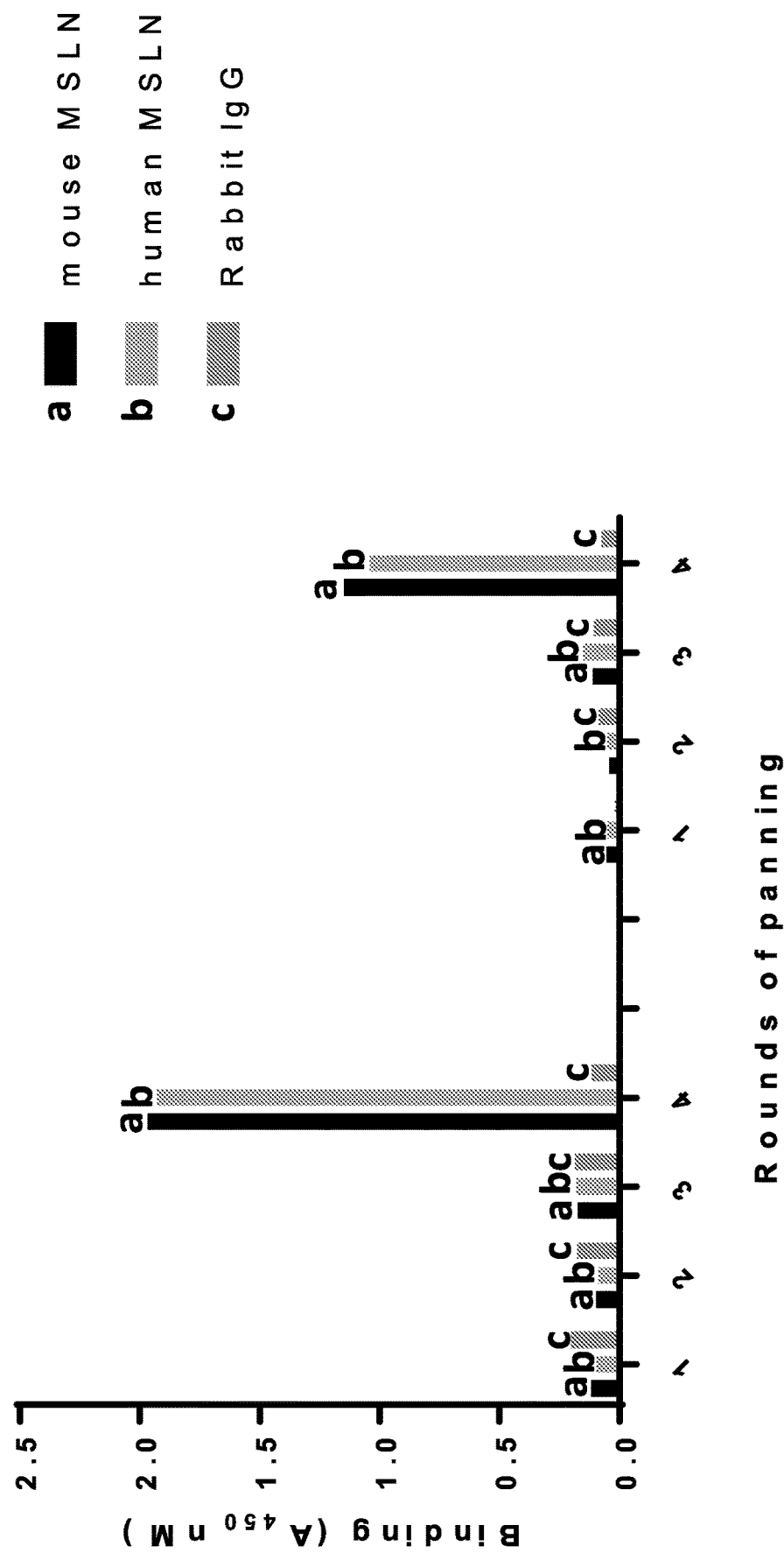
FIG. 1: Isolation of mesothelin-specific camel single domain antibodies by phage display. The graph shows the results of polyclonal phage ELISA to detect binding to mouse mesothelin and human mesothelin by the output phage of each round of panning. Bars on the left represent panning for isolation of A101. Bars on the right represent panning for isolation of G8. Both show strong binding to human and mouse mesothelin.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jul. 5, 2021, 14.5 KB, which is incorporated by reference herein. In the accompanying sequence listing:

SEQ ID NO: 1 is the nucleotide sequence of the A101 antibody.

SEQ ID NO: 2 is the amino acid sequence of the A101 antibody.

SEQ ID NO: 3 is the nucleotide sequence of the G8 antibody.

SEQ ID NO: 4 is the amino acid sequence of the G8 antibody.

SEQ ID NO: 5 is an exemplary GMCSFRss amino acid sequence.

SEQ ID NO: 6 is an exemplary CD8α hinge region amino acid sequence.

SEQ ID NO: 7 is an exemplary CD8α transmembrane region amino acid sequence.

SEQ ID NO: 8 is an exemplary 4-1BB amino acid sequence.

SEQ ID NO: 9 is an exemplary CD3ξ amino acid sequence.

SEQ ID NO: 10 is an exemplary self-cleaving T2A peptide amino acid sequence.

SEQ ID NO: 11 is an exemplary huEGFRt amino acid sequence.

SEQ ID NO: 12 is an exemplary human mesothelin amino acid sequence.

DETAILED DESCRIPTION

| Abbreviations | |
|---|---|
| ADC | antibody-drug conjugate |
| ADCC | antibody-dependent cell-mediated cytotoxicity |
| CAR | chimeric antigen receptor |
| CDR | complementarity determining region |
| CTL | cytotoxic T lymphocyte |
| E:T | effector to target |
| EGF | epidermal growth factor |
| EGFR | epidermal growth factor receptor |
| ELISA | enzyme-linked immunosorbent assay |
| FACS | fluorescence activated cells sorting |
| GMCSFRss | granulocyte-macrophage colony stimulating factor receptor signalsequence |
| huEGFRt | human truncated epidermal growth factor receptor |
| Ig | immunoglobulin |
| NK | natural killer |
| PE | *Pseudomonas* exotoxin |
| PET | positron emission tomography |

II. Summary of Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

4-1BB: A co-stimulatory molecule expressed by T cell receptor (TCR)-activated lymphocytes, and by other cells including natural killer cells. Ligation of 4-1BB induces a signaling cascade that results in cytokine production, expression of anti-apoptotic molecules and an enhanced immune response. An exemplary amino acid sequence of 4-1BB is set forth herein as SEQ ID NO: 8.

Administration: To provide or give a subject an agent, such as a such as an anti-mesothelin antibody provided herein, by any effective route. Exemplary routes of administration include, but are not limited to, oral, injection (such as subcutaneous, intramuscular, intradermal, intraperitoneal, intravenous, and intratumoral), sublingual, rectal, transdermal, intranasal, vaginal and inhalation routes.

Antibody: A polypeptide ligand comprising at least one variable region that recognizes and binds (such as specifically recognizes and specifically binds) an epitope of an antigen. Mammalian immunoglobulin molecules are composed of a heavy (H) chain and a light (L) chain, each of which has a variable region, termed the variable heavy ($V_H$) region and the variable light ($V_L$) region, respectively. Together, the $V_H$ region and the $V_L$ region are responsible for binding the antigen recognized by the antibody. There are five main heavy chain classes (or isotypes) of mammalian immunoglobulin, which determine the functional activity of an antibody molecule: IgM, IgD, IgG, IgA and IgE. Antibody isotypes not found in mammals include IgX, IgY, IgW and IgNAR. IgY is the primary antibody produced by birds and reptiles, and is functionally similar to mammalian IgG and IgE. IgW and IgNAR antibodies are produced by cartilaginous fish, while IgX antibodies are found in amphibians.

Antibody variable regions contain "framework" regions and hypervariable regions, known as "complementarity determining regions" or "CDRs." The CDRs are primarily responsible for binding to an epitope of an antigen. The framework regions of an antibody serve to position and align the CDRs in three-dimensional space. The amino acid sequence boundaries of a given CDR can be readily determined using any of a number of well-known numbering schemes, including those described by Kabat et al. (*Sequences of Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., JMB 273,927-948, 1997; the "Chothia" numbering scheme), Kunik et al. (see Kunik et al., *PLoS Comput Biol* 8:e1002388, 2012; and Kunik et al., *Nucleic Acids Res* 40 (Web Server issue): W521-524, 2012; "Paratome CDRs") and the ImMunoGeneTics (IMGT) database (see, Lefranc, *Nucleic Acids Res* 29:207-9, 2001; the "IMGT" numbering scheme). The Kabat, Paratome and IMGT databases are maintained online.

A "single-domain antibody" refers to an antibody having a single domain (a variable domain) that is capable of specifically binding an antigen, or an epitope of an antigen, in the absence of an additional antibody domain. Single-domain antibodies include, for example, $V_H$ domain antibodies, $V_{NAR}$ antibodies, camelid $V_H H$ antibodies, and $V_L$ domain antibodies. $V_{NAR}$ antibodies are produced by cartilaginous fish, such as nurse sharks, wobbegong sharks, spiny dogfish and bamboo sharks. Camelid $V_HH$ antibodies are produced by several species including camel, llama, alpaca, dromedary, and guanaco, which produce heavy chain antibodies that are naturally devoid of light chains.

A "monoclonal antibody" is an antibody produced by a single clone of lymphocytes or by a cell into which the coding sequence of a single antibody has been transfected. Monoclonal antibodies are produced by known methods. Monoclonal antibodies include humanized monoclonal antibodies.

A "chimeric antibody" has framework residues from one species, such as human, and CDRs (which generally confer antigen binding) from another species.

A "humanized" antibody is an immunoglobulin including a human framework region and one or more CDRs from a non-human (for example a mouse, rabbit, rat, shark or synthetic) immunoglobulin. The non-human immunoglobulin providing the CDRs is termed a "donor," and the human immunoglobulin providing the framework is termed an "acceptor." In one embodiment, all CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A humanized antibody binds to the same antigen as the donor antibody that provides the CDRs. Humanized or other monoclonal antibodies can have additional conservative amino acid substitutions which have substantially no effect on antigen binding or other immunoglobulin functions.

Antibody-drug conjugate (ADC): A molecule that includes an antibody (or antigen-binding fragment of an antibody) conjugated (such as covalently attached) to a drug, such as a cytotoxic agent. ADCs can be used to specifically target a drug to cancer cells through specific binding of the antibody to a tumor antigen expressed on the cell surface. Exemplary drugs for use with ADCs include anti-microtubule agents (such as maytansinoids, auristatin E and auristatin F) and interstrand crosslinking agents (for example, pyrrolobenzodiazepines; PDBs). In some cases, the ADC is a bi-specific ADC, which is comprised of two monoclonal antibodies or antigen-fragments thereof, each directed to a different antigen or epitope, conjugated to a drug.

Anti-microtubule agent: A type of drug that blocks cell growth by stopping mitosis. Anti-microtubule agents, also referred to as "anti-mitotic agents," are used to treat cancer.

Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. In other embodiments, antibody affinity is measured by flow cytometry or by surface plasmon reference. An antibody that "specifically binds" an antigen (such as mesothelin) is an antibody that binds the antigen with high affinity and does not significantly bind other unrelated antigens.

In some examples, an antibody or fragment thereof (such as an anti-mesothelin antibody provided herein) specifically binds to a target (such as a mesothelin) with a binding constant that is at least $10^1$ $M^{-1}$ greater, $10^4$ $M^{-1}$ greater or $10^5$ $M^{-1}$ greater than a binding constant for other molecules in a sample or subject. In some examples, an antibody (e.g., monoclonal antibody) or fragments thereof, has an equilibrium constant (Kd) of 1 nM or less. For example, an antibody or fragment thereof binds to a target, such as mesothelin with a binding affinity of at least about $0.1 \times 10^{-8}$ M, at least about $0.3 \times 10^{-8}$ M, at least about $0.5 \times 10^{-8}$ M, at least about $0.75 \times 10^{-8}$ M, at least about $1.0 \times 10^{-8}$ M, at least about $1.3 \times 10^{-8}$ M at least about $1.5 \times 10^{-8}$ M, or at least about $2.0 \times 10^{-8}$ M, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, or at least about $5.0 \times 10^{-8}$ M. In certain embodiments, a specific binding agent that binds to target has a dissociation constant (Kd) of $\leq 104$ nM, $\leq 100$ nM, $\leq 10$ nM, $\leq 1$ nM, $\leq 0.1$ nM, $\leq 0.01$ nM, or $\leq 0.001$ nM (e.g., $10^{-8}$M or less, e.g., from $10^{-8}$M to $10^{-13}$M, e.g., from $10^{-9}$ M to $10^{-13}$ M). In one embodiment, Kd is measured by a radiolabeled antigen binding assay (RIA) performed with the Fab version of an antibody of interest and its antigen (see, e.g., Chen et al., *J. Mol. Biol.* 293:865-881, 1999). In another example, Kd is measured using surface plasmon resonance assays using a BIACORES-2000 or a BIACORES-3000 (BIAcore, Inc., Piscataway, N.J.) at 25° C. with immobilized antigen CM5 chips at about 10 response units (RU).

Bispecific antibody: A recombinant protein that includes antigen-binding fragments of two different monoclonal antibodies (such as two single-domain antibodies), and is thereby capable of binding two different antigens. In some embodiments, bispecific antibodies are used for cancer immunotherapy by simultaneously targeting, for example, both CTLs (such as a CTL receptor component such as CD3) or effector natural killer (NK) cells, and a tumor antigen. Similarly, a multi-specific antibody is a recombinant protein that includes antigen-binding fragments of at least two different monoclonal antibodies, such as two, three or four different monoclonal antibodies (such as single-domain antibodies).

Breast cancer: A type of cancer that forms in tissues of the breast, usually the ducts (tubes that carry milk to the nipple) and lobules (glands that make milk). Triple negative breast cancer refers to a type of breast cancer in which the cancer cells do not express estrogen receptors, progesterone receptors or significant levels of HER2/neu protein. Triple negative breast cancer is also called ER-negative PR-negative HER2/neu-negative breast cancer.

Chemotherapeutic agent: Any chemical agent with therapeutic usefulness in the treatment of diseases characterized by abnormal cell growth. Such diseases include tumors, neoplasms, and cancer. In one embodiment, a chemotherapeutic agent is an agent of use in treating a mesothelin-positive tumor. In one embodiment, a chemotherapeutic agent is a radioactive compound. Exemplary chemotherapeutic agents that can be used with the methods provided herein are disclosed in Slapak and Kufe, *Principles of Cancer Therapy*, Chapter 86 in Harrison's Principles of Internal Medicine, 14th edition; Perry et al., *Chemotherapy*, Ch. 17 in Abeloff, *Clinical Oncology* $2^{nd}$ ed., © 2000 Churchill Livingstone, Inc; Baltzer, L., Berkery, R. (eds.): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody that binds mesothelin used in combination with a radioactive or chemical compound. In one example, a chemotherapeutic agent is a biologic, such as a therapeutic antibody (e.g., therapeutic monoclonal antibody), such as an anti-mesothelin antibody provided herein, as well as other anti-cancer antibodies, such as anti-PD1 or anti-PDL1 (e.g., pembrolizumab and nivolumab), anti-EGFR (e.g., cetuximab), or anti-VEGF (e.g., bevacizumab).

Chimeric antigen receptor (CAR): A chimeric molecule that includes an antigen-binding portion (such as a scFv or single-domain antibody) and a signaling domain, such as a signaling domain from a T cell receptor (for example, CD3ξ). Typically, CARs are comprised of an antigen-binding moiety, a transmembrane domain and an endodomain. The endodomain typically includes a signaling chain having an immunoreceptor tyrosine-based activation motif (ITAM), such as CD3ξ or FcεRIγ. In some instances, the endodomain further includes the intracellular portion of at least one additional co-stimulatory domain, such as CD28, 4-1BB (CD137), ICOS, OX40 (CD134), CD27 and/or DAP10. In some examples, the CAR is bispecific or bicistronic. A bispecific CAR is a single CAR molecule comprised of two antigen-binding domains (such as two scFv or two single-domain antibodies) that each bind a different antigen. A bicistronic CAR refers to two complete CAR molecules, each containing an antigen-binding moiety that binds a different antigen. In some cases, a bicistronic CAR construct expresses two complete CAR molecules that are linked by a cleavage linker. T cells or NK cells expressing a bispecific or bicistronic CAR can bind cells that express both of the antigens to which the binding moieties are directed (see, for example, Qin et al., *Blood* 130:810, 2017; and WO/2018/213337).

Cholangiocarcinoma: A type of cancer that develops in cells that line the bile ducts in the liver.

Complementarity determining region (CDR): A region of hypervariable amino acid sequence that defines the binding affinity and specificity of an antibody. The light and heavy chains of a mammalian immunoglobulin each have three CDRs, designated L-CDR1, L-CDR2, L-CDR3 and H-CDR1, H-CDR2, H-CDR3, respectively. A single-domain antibody contains three CDRs, referred to herein as CDR1, CDR2 and CDR3.

Conjugate: In the context of the present disclosure, a "conjugate" is an antibody or antibody fragment (such as an antigen-binding fragment) covalently linked to an effector molecule or a second protein (such as a second antibody). The effector molecule can be, for example, a drug, toxin, therapeutic agent, detectable label, protein, nucleic acid, lipid, nanoparticle, photon absorber, carbohydrate or recombinant virus. An antibody conjugate is often referred to as an "immunoconjugate." When the conjugate comprises an antibody linked to a drug (such as a cytotoxic agent), the conjugate is often referred to as an "antibody-drug conjugate" or "ADC." Other antibody conjugates include, for example, multi-specific (such as bispecific or trispecific) antibodies and chimeric antigen receptors (CARs).

Conservative variant: A protein containing conservative amino acid substitutions that do not substantially affect or decrease the affinity of a protein, such as an antibody to mesothelin. For example, a monoclonal antibody that specifically binds mesothelin can include at most about 1, at most about 2, at most about 5, and most about 10, or at most about 15 conservative substitutions and specifically bind the mesothelin polypeptide. The term "conservative variant" also includes the use of a substituted amino acid in place of an unsubstituted parent amino acid, provided that antibody specifically binds mesothelin. Non-conservative substitutions are those that reduce an activity or binding to mesothelin.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Contacting: Placement in direct physical association; includes both in solid and liquid form.

Cytotoxic agent: Any drug or compound that kills cells.

Cytotoxicity: The toxicity of a molecule, such as an immunotoxin, to the cells intended to be targeted, as opposed to the cells of the rest of an organism. In contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Diagnostic: Identifying the presence or nature of a pathologic condition, such as a mesothelin-positive cancer. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (such as severity) of a pathologic condition, such as mesothelioma.

Diagnostic tumor imaging: Coupling antibodies and their derivatives with positron emitting radionuclides for positron emission tomography (PET) is a process often referred to as immunoPET. While full length antibodies can be used as immunoPET agents, their biological half-life can require waiting several days prior to imaging, resulting in an increase in non-target radiation doses. Smaller, single domain antibodies have biological half-lives amenable to same day imaging.

Drug: Any compound used to treat, ameliorate or prevent a disease or condition in a subject. In some embodiments herein, the drug is an anti-cancer agent, for example a cytotoxic agent, such as an anti-mitotic or anti-microtubule agent.

Effector molecule: The portion of a chimeric molecule that is intended to have a desired effect on a cell to which the chimeric molecule is targeted. Effector molecule is also known as an effector moiety (EM), therapeutic agent, diagnostic agent, or similar terms. Therapeutic agents (or drugs) include such compounds as nucleic acids, proteins, peptides, amino acids or derivatives, glycoproteins, radioisotopes, photon absorbers, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-mesothelin antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies or other therapeutic agents are known (see, for example, U.S. Pat. No. 4,957,735; and Connor et al, *Pharm Ther* 28:341-365, 1985). Diagnostic agents or moieties include radioisotopes and other detectable labels. Detectable labels useful for such purposes include radioactive isotopes such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$ $^{99}Tc$, $^{111}In$ and $^{125}I$, fluorophores, chemiluminescent agents, and enzymes.

Epitope: An antigenic determinant. These are particular chemical groups or peptide sequences on a molecule that are antigenic (that elicit a specific immune response). An antibody specifically binds a particular antigenic epitope on a polypeptide, such as mesothelin.

Framework region: Amino acid sequences interposed between CDRs. Framework regions of an immunoglobulin molecule include variable light and variable heavy framework regions.

Fusion protein: A protein comprising at least a portion of two different (heterologous) proteins.

Heterologous: Originating from a separate genetic source or species.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a $CD4^+$ response or a $CD8^+$ response. In another embodiment, the response is a B cell response, and results in the production of specific antibodies.

Immunoconjugate: A covalent linkage of an effector molecule to an antibody or functional fragment thereof. The effector molecule can be, for example, a detectable label, a photon absorber (such as IR700), or a toxin (to form an immunotoxin, such as an immunotoxin comprising *Pseudomonas* exotoxin or a variant thereof). Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody. In one embodiment, an antibody is joined to an effector molecule. In another embodiment, an antibody joined to an effector molecule is further joined to a lipid or other molecule, such as to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand or an antibody, conjugated (coupled) to an effector molecule. The term "conjugated" or "linked" refers to making two polypeptides into one contiguous polypeptide molecule.

Immunoliposome: A liposome with antibodies or antibody fragments conjugated to its surface. Immunoliposomes can carry cytotoxic agents or other drugs to antibody-targeted cells, such as tumor cells.

Interstrand crosslinking agent: A type of cytotoxic drug capable of binding covalently between two strands of DNA, thereby preventing DNA replication and/or transcription.

Isolated: An "isolated" biological component, such as a nucleic acid, protein (including antibodies) or organelle, has been substantially separated or purified away from other biological components in the environment (such as a cell) in which the component naturally occurs, for example other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, $^{11}C$, $^{13}N$, $^{15}O$, $^{18}F$, $^{19}F$, $^{99m}Tc$, 131I, $^{3}H$, $^{14}C$, $^{15}N$, $^{90}Y$ $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label. The terms "conjugating," "joining," "bonding" or "linking" refer to making two polypeptides into one contiguous polypeptide molecule, or to covalently attaching a radionuclide or other molecule to a polypeptide, such as an antibody. The linkage can be either by chemical or recombinant means. "Chemical means" refers to a reaction between the antibody moiety and the effector molecule such that there is a covalent bond formed between the two molecules to form one molecule.

Lung cancer: Cancer that forms in tissues of the lung, usually in the cells lining air passages. The two main types are small cell lung cancer and non-small cell lung cancer (NSCLC). These types can be diagnosed using microscopy.

Mesothelin: A 40 kDa cell-surface glycosylphosphatidylinositol (GPI)-linked glycoprotein. The human mesothelin protein is synthesized as a 70 kD precursor which is then proteolytically processed. The 30 kD amino terminus of mesothelin is secreted and is referred to as megakaryocyte potentiating factor (Yamaguchi et al., *J. Biol. Chem.* 269:805 808, 1994). The 40 kD carboxyl terminus remains bound to the membrane as mature mesothelin (Chang et al., *Natl. Acad. Sci.* USA 93:136 140, 1996). Exemplary nucleic acid and amino acid sequences of mesothelin are as described in PCT Publication No. WO 97/25,068; U.S. Pat. No. 6,083, 502; Chang and Pastan, *Int. J. Cancer* 57:90, 1994; Chang and Pastan, *Proc. Natl. Acad. Sci USA* 93:136, 1996; Brinkmann et al., *Int. J. Cancer* 71:638, 1997; and Chowdhury et al., *Mol. Immunol.* 34:9, 1997. An exemplary amino acid sequence of human mesothelin is set forth herein as SEQ ID NO: 12 (see also GenBank Accession No. AAH09272). Mesothelin also refers to mesothelin proteins or polypeptides which remain intracellular as well as secreted and/or isolated extracellular mesothelin protein.

Mesothelioma: A type of neoplasm derived from the cells lining the pleura and peritoneum, which grow as a thick sheet covering the viscera. The lining is composed of spindle cells or fibrous tissue which may enclose gland-like spaces lined by cuboidal cells. Mesotheliomas often originate in the tissue lining the lung, heart or abdomen. In some cases, mesotheliomas are caused by exposure to asbestos.

Mesothelin-positive cancer: A cancer that expresses or overexpresses mesothelin. Examples of mesothelin-positive cancers include, but are not limited to, mesothelioma, prostate cancer, lung cancer, stomach cancer, squamous cell carcinoma, pancreatic cancer, cholangiocarcinoma, breast cancer (such as triple negative breast cancer) and ovarian cancer.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Ovarian cancer: Cancer that forms in tissues of the ovary (one of a pair of female reproductive glands in which the ova, or eggs, are formed). Most ovarian cancers are either ovarian epithelial carcinomas (cancer that begins in the cells on the surface of the ovary) or malignant germ cell tumors (cancer that begins in egg cells).

Pancreatic cancer: A disease in which malignant (cancer) cells are found in the tissues of the pancreas. Also called exocrine cancer.

Pharmaceutically acceptable carriers: The pharmaceutically acceptable carriers of use are conventional. *Remington's Pharmaceutical Sciences*, by E. W. Martin, Mack Publishing Co., Easton, PA, 15th Edition, 1975, describes compositions and formulations suitable for pharmaceutical delivery of the antibodies and other compositions disclosed herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Photoimmunotherapy: A targeted cancer therapy that utilizes an antigen-specific antibody-photoabsorber conjugate that can be activated by near-infrared light to kill targeted cells. The photon absorber is typically based on phthalocyanine dye, such as a near infrared (NIR) phthalocyanine dye (for example, IRDye® 700DX, also known knows as IR700). The antibody (for example, a mesothelin-specific antibody) binds to the appropriate cell surface antigen (e.g. mesothelin) and the photo-activatable dye induces lethal damage to cell membranes after NIR-light exposure. NIR-light exposure (690 nm) induces highly selective, necrotic cancer cell death within minutes without damage to adjoining cells (see, for example, U.S. Application No. 2018/0236076). Thus provided herein are the disclosed antibodies (e.g., A101 and G8, or fragments thereof) conjugated to IR700.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Prostate cancer: Cancer that forms in tissues of the prostate (a gland in the male reproductive system found below the bladder and in front of the rectum). Prostate cancer usually occurs in older men.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein, such as an antibody or antibody fragment, is 90% free of other proteins or cellular components.

Pyrrolobenzodiazepine (PBD): A class of sequence-selective DNA minor-groove binding crosslinking agents originally discovered in *Streptomyces* species. PDBs are significantly more potent than systemic chemotherapeutic drugs. The mechanism of action of PBDs is associated with their ability to form an adduct in the minor groove of DNA, thereby interfering with DNA processing. In the context of the present disclosure, PBDs include naturally produced and isolated PBDs, chemically synthesized naturally occurring PBDs, and chemically synthesized non-naturally occurring PBDs. PBDs also include monomeric, dimeric and hybrid PBDs (for a review see Gerratana, *Med Res Rev* 32(2):254-293, 2012).

Recombinant: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material. In one example, a sample includes a tumor biopsy. In one example, a sample includes a fine needle aspirate.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Homologs and variants of a $V_H$ domain of an antibody that specifically binds a mesothelin polypeptide are typically characterized by possession of at least about 75%, for example at least about 80%, 90%, 95%, 96%, 97%, 98% or 99% sequence identity counted over the full-length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of $10^{-20}$ amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Small molecule: A molecule, typically with a molecular weight less than about 1000 Daltons, or in some embodiments, less than about 500 Daltons, wherein the molecule is capable of modulating, to some measurable extent, an activity of a target molecule.

Squamous cell carcinoma: A malignant neoplasm derived from stratified squamous epithelium, but which may also occur in sites such as bronchial mucosa where glandular or columnar epithelium is normally present. Squamous cell carcinoma is the most common type of skin cancer.

Stomach cancer: Cancer that forms in tissues lining the stomach. Also called gastric cancer.

Subject: Living multi-cellular vertebrate organisms, a category that includes both human and veterinary subjects, including human and non-human mammals.

Synthetic: Produced by artificial means in a laboratory, for example a synthetic nucleic acid or protein (for example, an antibody) can be chemically synthesized in a laboratory.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate, reduce the size, or prevent metastasis of a tumor, such as reduce a tumor size and/or volume by at least 10%, at least 20%, at least 50%, at least 75%, at least 80%, at least 90%, at least 95%, or even 100%, and/or reduce the number and/or size/volume of metastases by at least 10%, at least 20%, at least 50%, at least 75%, at least 80%, at least 90%, at least 95%, or even 100%, for example as compared to a size/volume/number prior to treatment. When administered to a subject, a dosage will generally be used that will achieve target tissue concentrations (for example, in tumors) that has been shown to achieve a desired in vitro effect.

Toxin: A molecule that is cytotoxic for a cell. Toxins include abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art. In some embodiments, the vector is a virus vector, such as a lentivirus vector or an AAV vector.

III. Monoclonal Antibodies Specific for Mesothelin

Described herein are two cross species mesothelin-specific camel single-domain monoclonal antibodies isolated by phage display. The disclosed mesothelin-specific antibodies, A101 and G8, specifically bind both human and mouse mesothelin with high affinity. Chimeric antigen receptor (CAR) T cells comprised of the disclosed antibodies are capable of potently killing mesothelin-positive tumor cells in vitro and in vivo. The nucleotide and amino acid sequences of A101 and G8 are provided below. Tables 1 and 2 list the amino acid positions of CDR1, CDR2 and CDR3 of each antibody, as determined using either Kabat, IMGT, or Paratome, or a combination of all three. One of skill in the art could readily determine the CDR boundaries using an alternative numbering scheme, such as the Chothia numbering scheme.

A101 DNA
(SEQ ID NO: 1)
CAGGTGCAGCTGGTGGAGTCTGGGGGCGGCACGGTGCAGGCTGGAGGGT

CGCTGAAACTCGCCTGCGCAGCCTCTGGATTACCCAGAACGTACAATGT

CATGGGCTGGTTCCGCCAGGCCCCAGGGAAGGAGCGCGAGGGGGTCGCA

ATAATTTATACTACGACTGGAGCAACATACTATCGCGACTCCGTCAAGG

GCCGGGCCACCATCTCCCAAGACAACGCCAAGAAGTCGGTGTCTCTCCA

AATGAACAGCCTGAGGCCTGAGGACACGGCCATCTATTACTGTGTGGCT

AGGCAACCCAATAGTGGTCCCTGGGAGTATTGGGGCCAGGGGACCCAGG

TCACCGTCTCCTCA

A101 protein
(SEQ ID NO: 2)
QVQLVESGGGTVQAGGSLKLACAASGLPRTYNVMGWFRQAPGKEREGVA

IIYTTTGATYYRDSVKGRATISQDNAKKSVSLQMNSLRPEDTAIYYCVA

RQPNSGPWEYWGQGTQVTVSS (Underline = Kabat CDRs; Bold = IMGT CDRs;
Italics = Paratome CDRs)

TABLE 1

Location of CDRs in the A101 amino acid sequence (SEQ ID NO: 2)

| Numbering Scheme | CDR1 | CDR2 | CDR3 |
|---|---|---|---|
| Kabat | 31-35 | 50-66 | 99-108 |
| IMGT | 26-33 | 51-58 | 97-108 |
| Paratome | 27-35 | 47-61 | 97-108 |
| Combined | 26-35 | 47-66 | 97-108 |

G8 DNA
(SEQ ID NO: 3)
CAGGTAAAGCTGGAGGAGTCTGGGGGAGGCTCGGTGCAGGCTGGAGGGT

CTCTGAGACTCTCCTGTACAACTTCTGGATACACCAACAGTTACAAGTG

GATGGGCTGGTTCCGCCAGGCTCCAGGACAAGAGCGCGAGGGGGTCGCA

GTTATTTACACCGGTAATGATAGGACATACTATAGTGACTCCGTGAAGG

GCCGATTCACCATCTCCCGAGACAACGCCAAGAATATGATCTATCTGGA

CATGACGCGCCTGAGACCTGAGGACAGCGCTGTGTACGAGTGTGCCATC

GGACATGATGGCGCATGGCGTTACTGGGGCCAGGGAACGCAGGTCACCG

TCTCCTCA

G8 protein
(SEQ ID NO: 4)
QVKLEESGGGSVQAGGSLRLSCTTSGYTNSYKWMGWFRQAPGQEREGVA

VIYTGNDRTYYSDSVKGRFTISRDNAKNMIYLDMTRLRPEDSAVYECAI

GHDGAWRYWGQGTQVTVSS (Underline = Kabat CDRs; Bold = IMGT CDRs;
Italics = Paratome CDRs)

TABLE 2

Location of CDRs in the G8 amino acid sequence (SEQ ID NO: 4)

| Numbering Scheme | CDR1 | CDR2 | CDR3 |
|---|---|---|---|
| Kabat | 31-35 | 50-66 | 99-106 |
| IMGT | 26-33 | 51-58 | 97-106 |
| Paratome | 27-35 | 47-60 | 98-106 |
| Combined | 26-35 | 47-66 | 97-106 |

Provided herein are single-domain (VHH) monoclonal antibodies that bind (for example, specifically bind) mesothelin, such as cell-surface or soluble mesothelin. In some embodiments, the mesothelin is human mesothelin, mouse mesothelin, or both human and mouse mesothelin. In some embodiments, the antibody comprises at least a portion of the amino acid sequence set forth herein as SEQ ID NO: 2 or SEQ ID NO: 4, such as one or more (such as all three) CDR sequences from SEQ ID NO: 2 or SEQ ID NO: 4, as determined by any numbering scheme, such as IMGT, Kabat, Paratome or Chothia.

In some embodiments, the monoclonal antibody comprises the CDR1, CDR2 and CDR3 sequences of SEQ ID NO: 2. In some examples, the CDR sequences are determined using the IMGT, Kabat, Paratome or Chothia numbering scheme, or a combination thereof. In particular examples, the CDR sequences are determined using a combination of Kabat, IMGT and Paratome.

In some embodiments, the monoclonal antibody comprises the CDR1, CDR2 and CDR3 sequences of SEQ ID NO: 4. In some examples, the CDR sequences are determined using the IMGT, Kabat, Paratome or Chothia numbering scheme, or a combination thereof. In particular examples, the CDR sequences are determined using a combination of Kabat, IMGT and Paratome.

In some embodiments, the CDR1, CDR2 and CDR3 sequences of the monoclonal antibody comprise residues 31-35, 50-66 and 99-108 of SEQ ID NO: 2; residues 26-33, 51-58 and 97-108 of SEQ ID NO: 2; residues 27-35, 47-61 and 97-108 of SEQ ID NO: 2; or residues 26-35, 47-66 and 97-108 of SEQ ID NO: 2. In some examples, the amino acid sequence of the monoclonal antibody is at least 80%, at least 85%, at least 90%, at least 95%, at least 96%, at least 97%, at least 98% or at least 99% identical to SEQ ID NO: 2. In specific non-limiting examples, the sequence of the monoclonal antibody comprises or consists of SEQ ID NO: 2.

In some embodiments, the CDR1, CDR2 and CDR3 sequences of the monoclonal antibody comprise residues 31-35, 50-66 and 99-106 of SEQ ID NO: 4; residues 26-33, 51-58 and 97-106 of SEQ ID NO: 4; residues 27-35, 47-60 and 98-106 of SEQ ID NO: 4; or residues 26-35, 47-66 and 97-106 of SEQ ID NO: 4. In some examples, the amino acid sequence of the monoclonal antibody is at least 80%, at least 85%, at least 90%, at least 95%, at least 96%, at least 97%, at least 98% or at least 99% identical to SEQ ID NO: 4. In specific non-limiting examples, the sequence of the monoclonal antibody comprises of consists of SEQ ID NO: 4.

In some embodiments, the monoclonal antibody is a camel antibody. In some embodiments, the monoclonal antibody is a humanized antibody. In some embodiments, the monoclonal antibody is a chimeric antibody.

Also provided herein are chimeric antigen receptors (CARs) that include a monoclonal antibody disclosed herein. In some embodiments, the CAR further includes a hinge region, a transmembrane domain, a costimulatory signaling moiety, a signaling domain, or any combination thereof. In specific non-limiting examples, the hinge region comprises a CD8α hinge region, the transmembrane domain comprises a CD8α transmembrane domain, the costimulatory signaling moiety comprises a 4-1BB signaling moiety and/or the signaling domain comprises a CD3ξ signaling domain.

Further provided are cells expressing a mesothelin-specific CAR. In some examples, the cell is a T lymphocyte, such as a CTL. CARs and CAR-expressing T cells are further described in section IV.

Also provided herein are immunoconjugates that include a monoclonal antibody disclosed herein and an effector molecule. In some embodiments, the effector molecule is a toxin, such as, but not limited to, *Pseudomonas* exotoxin or a variant thereof, such as PE38. In other embodiments, the effector molecule is a detectable label, such as, but not limited to, a fluorophore, an enzyme or a radioisotope. In other embodiments, the effector molecule is a photon absorber, such as IR700. Immunoconjugates comprising a photon absorber can be used for photoimmunotherapy. Immunoconjugates are further described in section V.

Further provided herein are antibody-drug conjugates (ADCs) that include a drug conjugated to a monoclonal antibody disclosed herein. In some embodiments, the drug is a small molecule, for example an anti-microtubule agent, an anti-mitotic agent and/or a cytotoxic agent. ADCs are further described in section VI.

Also provided herein are multi-specific antibodies that include a monoclonal antibody disclosed herein and at least one additional monoclonal antibody or antigen-binding fragment thereof. In some embodiments, the multi-specific antibody is a bispecific antibody. In other embodiments, the multi-specific antibody is a trispecific antibody. In some embodiments, the at least one additional monoclonal antibody or antigen binding fragment thereof specifically binds a component of the T cell receptor or a natural killer (NK) cell activating receptor. Multi-specific antibodies are further described in section VII.

Further provided herein are antibody-nanoparticle conjugates that include a nanoparticle conjugated to a monoclonal antibody disclosed herein. In some embodiments, the nanoparticle comprises a polymeric nanoparticle, nanosphere, nanocapsule, liposome, dendrimer, polymeric micelle, or niosome. In some embodiments, the nanoparticle includes a cytotoxic agent. Antibody-nanoparticle conjugates are further described in section VIII.

Also provided herein are fusion proteins that include a monoclonal antibody disclosed herein and a heterologous protein or peptide. In some embodiments, the heterologous protein is an Fc protein. In some examples, the Fc protein is a mouse Fc or a human Fc protein.

Also provided are nucleic acid molecules encoding a monoclonal antibody disclosed herein. In some embodiments, the nucleic acid molecule is at least 80%, at least 85%, at least 90%, at least 95%, at least 96%, at least 97%, at least 98% or at least 99% identical to SEQ ID NO: 1 or SEQ ID NO: 3. In some examples, the nucleic acid molecule comprises of consists of SEQ ID NO: 1 or SEQ ID NO: 3, or a degenerate variant thereof. Further provided are nucleic acid molecules encoding a CAR, immunoconjugate, multi-specific antibody, or fusion protein disclosed herein. In some embodiments, the nucleic acid molecule is operably linked to a promoter. Vectors that include the nucleic acid molecules are further provided herein.

Further provided herein is a nucleic acid construct that expresses a CAR and a truncated human EGFR (huEGFRt). In some embodiments, the nucleic acid comprises in the 5' to 3' direction: a nucleic acid encoding a first granulocyte-macrophage colony stimulating factor receptor signal sequence (GMCSFRss); a nucleic acid encoding a mesothelin-specific monoclonal antibody disclosed herein; a nucleic acid encoding an extracellular hinge region; a nucleic acid encoding a transmembrane domain; a nucleic acid encoding an intracellular co-stimulatory domain; a nucleic acid encoding a intracellular signaling domain; a nucleic acid encoding a self-cleaving 2A peptide; a nucleic acid encoding a second GMCSFRss; and a nucleic acid encoding a truncated human epidermal growth factor receptor (huEGFRt). In some examples, the nucleic acid further includes a human elongation factor 1α (EF1α) promoter sequence 5' of the nucleic acid encoding the first GMCSFRss. In some examples, the hinge region comprises a CD8α hinge region. In some examples, the transmembrane domain comprises a CD8α transmembrane domain. In some examples, the costimulatory signaling moiety comprises a 4-1BB signaling moiety. In some examples, the signaling domain comprises a CD3ξ signaling domain. In some examples, the amino acid sequence of the mesothelin-specific monoclonal antibody comprises of consists of SEQ ID NO: 2 or SEQ ID NO: 4. Vectors comprising the nucleic acid constructs are also provided. In some embodiments, the vector is a lentiviral vector.

Also provided is an isolated cell co-expressing a mesothelin-specific CAR disclosed herein and huEGFRt. In some examples, the cell is a cytotoxic T lymphocyte (CTL).

Compositions that include a pharmaceutically acceptable carrier and a monoclonal antibody CAR, isolated cell (such as a CAR expressing cell, for example a CAR T cell or a CAR NK cell), immunoconjugate, ADC, multi-specific antibody, antibody-nanoparticle conjugate, or fusion protein disclosed herein are further provided by the present disclosure. Compositions and their use are further described in section IX.

IV. Chimeric Antigen Receptors (CARs)

The disclosed monoclonal antibodies can also be used to produce CARs (also known as chimeric T cell receptors, artificial T cell receptors or chimeric immunoreceptors) and/or cytotoxic T lymphocytes (CTLs) or natural killer (NK) cells engineered to express CARs. Generally, CARs include a binding moiety, an extracellular hinge and spacer element, a transmembrane region and an endodomain that performs signaling functions (Cartellieri et al., *J Biomed Biotechnol* 2010:956304, 2010; Dai et al., *J Natl Cancer Inst* 108(7):djv439, 2016). In many instances, the binding moiety is an antigen binding fragment of a monoclonal antibody, such as a scFv, or a single-domain antibody. The spacer/hinge region typically includes sequences from IgG subclasses, such as IgG1, IgG4, IgD and CD8 domains. The transmembrane domain can be derived from a variety of different T cell proteins, such as CD3ξ, CD4, CD8 or CD28. Several different endodomains have been used to generate CARs. For example, the endodomain can consist of a signaling chain having an ITAM, such as CD3ξ or FcεRIγ. In some instances, the endodomain further includes the intracellular portion of at least one additional co-stimulatory domain, such as CD28, 4-1BB (CD137, TNFRSF9), OX-40 (CD134), ICOS, CD27 and/or DAP10.

CTLs, NK cells (or other immune cells) expressing CARs can be used to target a specific cell type, such as a mesothelin-positive tumor cell. Thus, the monoclonal antibodies disclosed herein can be used to engineer CTLs or NK cells that express a CAR containing the mesothelin-specific monoclonal antibody, thereby targeting the engineered CTLs or NK cells to mesothelin-expressing tumor cells.

Engineered T cells have previously been used for adoptive therapy for some types of cancer (see, for example, Park et al., *Mol Ther* 15(4):825-833, 2007). The use of T cells expressing CARs is more universal than standard CTL-based immunotherapy because CTLs expressing CARs are HLA unrestricted and can therefore be used for any patient having a tumor that expresses the target antigen.

Bispecific or bicistronic CARs are also contemplated by the present disclosure. In some embodiments, the bispecific CAR includes a single-domain antibody specific for mesothelin (such as A101 or G8) and a single-domain antibody specific for a different antigen. Similarly, a bicistronic CAR includes two CAR molecules expressed from the same construct where one CAR molecule is a mesothelin-targeted CAR and the second CAR targets a second antigen. See, for example, Qin et al., *Blood* 130:810, 2017; and WO/2018/213337.

Accordingly, provided herein are CARs that include a mesothelin-specific antibody. Also provided are isolated nucleic acid molecules and vectors encoding the CARs (including bispecific and bicistronic CARs), and host cells, such as CTLs or NK cells, expressing the CARs, bispecific CAR or bicistronic CARs. CTLs or NK cells expressing CARs comprised of a mesothelin-specific monoclonal antibody can be used for the treatment of cancers that express mesothelin. In some embodiments herein, the CAR is a bispecific CAR. In other embodiments herein, the CAR is a bicistronic CAR.

In some embodiments, the CAR includes a signal peptide sequence, for example, N-terminal to the antigen binding domain. The signal peptide sequence can be any suitable signal peptide sequence, such as a signal sequence from granulocyte-macrophage colony-stimulating factor receptor (GMCSFR), immunoglobulin light chain kappa, or IL-2. While the signal peptide sequence may facilitate expression of the CAR on the surface of the cell, the presence of the signal peptide sequence in an expressed CAR is not necessary in order for the CAR to function. Upon expression of the CAR on the cell surface, the signal peptide sequence may be cleaved off of the CAR. Accordingly, in some embodiments, the CAR lacks a signal peptide sequence.

In some embodiments, the CARs disclosed herein are expressed from a construct (such as from a lentivirus vector) that also expresses a truncated version of human EGFR (huEGFRt). The CAR and huEGFRt are separated by a self-cleaving peptide sequence (such as T2A) such that upon expression in a transduced cell, the CAR is cleaved from huEGFRt.

In some embodiments disclosed herein, the CAR constructs encode the following amino acid sequences, in the N-terminal to C-terminal direction:

GMCSFRss:
(SEQ ID NO: 5)
MLLLVTSLLLCELPHPAFLLIP

NdeI: HM
Antigen-binding: a mesothelin-specific antibody
(such as SEQ ID NO: 2 or SEQ ID NO: 4)
SpeI: TS CD8α hinge:
(SEQ ID NO: 6)
TTTPAPRPPTPAPTIASQPLSLRPEACRPAAGGAVHTRGLDFACD

CD8α TM:
(SEQ ID NO: 7)
IYIWAPLAGTCGVLLLSLVIT

-continued 4-1BB:
(SEQ ID NO: 8)
KRGRKKLLYIFKQPFMRPVQTTQEEDGCSCRFPEEEEGGCEL

CD3ζ:
(SEQ ID NO: 9)
RVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATK

DTYDALHMQALPPR

T2A:
(SEQ ID NO: 10)
EGRGSLLTCGDVEENPGP

GMCSFRss:
(SEQ ID NO: 5)
MLLLVTSLLLCELPHPAFLLIP huEGFRt:
(SEQ ID NO: 11)
RKVCNGIGIGEFKDSLSINATNIKHFKNCTSISGDLHILPVAFRGDSFT

HTPPLDPQELDILKTVKEITGFLLIQAWPENRTDLHAFENLEIIRGRTK

QHGQFSLAVVSLNITSLGLRSLKEISDGDVIISGNKNLCYANTINWKKL

FGTSGQKTKIISNRGENSCKATGQVCHALCSPEGCWGPEPRDCVSCRNV

SRGRECVDKCNLLEGEPREFVENSECIQCHPECLPQAMNITCTGRGPDN

CIQCAHYIDGPHCVKTCPAGVMGENNTLVWKYADAGHVCHLCHPNCTYG

CTGPGLEGCPTNGPKIPSIATGMVGALLLLLVVALGIGLFM

The human epidermal growth factor receptor is comprised of four extracellular domains, a transmembrane domain and three intracellular domains. The EGFR domains are found in the following N-terminal to C-terminal order: Domain I—Domain II—Domain III—Domain IV—transmembrane (TM) domain—juxtamembrane domain—tyrosine kinase domain—C-terminal tail. Domain I and Domain III are leucine-rich domains that participate in ligand binding. Domain II and Domain IV are cysteine-rich domains and do not make contact with EGFR ligands. Domain II mediates formation of homo- or hetero-dimers with analogous domains from other EGFR family members, and Domain IV can form disulfide bonds with Domain II. The EGFR™ domain makes a single pass through the cell membrane and may play a role in protein dimerization. The intracellular domain includes the juxtamembrane domain, tyrosine kinase domain and C-terminal tail, which mediate EGFR signal transduction (Wee and Wang, *Cancers* 9(52), doi:10.3390/cancers9050052; Ferguson, *Annu Rev Biophys* 37:353-373, 2008; Wang et al., *Blood* 118(5):1255-1263, 2011).

A truncated version of human EGFR, referred to herein as "huEGFRt" includes only Domain III, Domain IV and the TM domain. Thus, huEGFRt lacks Domain I, Domain II, and all three intracellular domains. huEGFRt is not capable of binding EGF and lacks signaling activity. However, this molecule retains the capacity to bind particular EGFR-specific monoclonal antibodies, such as FDA-approved cetuximab (PCT Publication No. WO 2011/056894, which is herein incorporated by reference).

Transduction of T cells (or NK cells) with a construct (such as a lentivirus vector) encoding both huEGFRt and a tumor antigen-specific CAR disclosed herein allows for selection of transduced T cells using labelled EGFR monoclonal antibody cetuximab (ERBITUX™). For example, cetuximab can be labeled with biotin, and transduced T cells can be selected using anti-biotin magnetic beads, which are commercially available (such as from Miltenyi Biotec). Co-expression of huEGFRt also allows for in vivo tracking of adoptively transferred CAR-expressing T cells (or NK cells). Furthermore, binding of cetuximab to T cells expressing huEGFRt induces cytotoxicity of ADCC effector cells, thereby providing a mechanism to eliminate transduced T cells in vivo (Wang et al., *Blood* 118(5):1255-1263, 2011), such as at the conclusion of therapy.

V. Immunoconjugates

The disclosed monoclonal antibodies can be conjugated to a therapeutic agent or effector molecule. Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents can include various drugs such as vinblastine, daunomycin and the like, cytotoxins such as native or modified *Pseudomonas* exotoxin or diphtheria toxin, encapsulating agents (such as liposomes) that contain pharmacological compositions, radioactive agents such as $^{125}$I, $^{32}$P, $^{14}$C, $^{3}$H and $^{35}$S, photon absorbers such as IR700, and other labels, target moieties and ligands.

The choice of a particular therapeutic agent depends on the particular target molecule or cell, and the desired biological effect. Thus, for example, the therapeutic agent can be a cytotoxin that is used to bring about the death of a particular target cell (such as a tumor cell). Conversely, where it is desired to invoke a non-lethal biological response (such as for use in detection), the therapeutic agent can be conjugated to a non-lethal pharmacological agent or a liposome containing a non-lethal pharmacological agent.

With the therapeutic agents and antibodies described herein, one of skill can readily construct a variety of clones containing functionally equivalent nucleic acids, such as nucleic acids which differ in sequence but which encode the same effector moiety or antibody sequence. Thus, the present disclosure provides nucleic acids encoding antibodies and conjugates and fusion proteins thereof.

Effector molecules can be linked to an antibody of interest using any number of means. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of known linker molecules. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, labels (such as enzymes or fluorescent molecules), drugs, toxins, and other agents to antibodies one skilled in the art will be able to determine a suitable method for attaching a given agent to an antibody or other polypeptide.

The antibodies disclosed herein can be derivatized or linked to another molecule (such as another peptide or protein). In general, the antibodies or portion thereof is derivatized such that the binding to the target antigen is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a photon absorber, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available.

The antibody can be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, green fluorescent protein (GFP) and yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect expression of a target antigen by x-ray, emission spectra, or other diagnostic techniques. Examples of labels for polypeptides include, but are not limited to, the following radioisotopes or radionucleotides: $^{3}H$, $^{14}C$, $^{15}N$, $^{35}S$, $^{90}Y$ $^{99}Tc$, $^{111}In$, $^{125}I$, 131I.

An antibody disclosed herein can also be conjugated to a photon absorber. In some embodiments, the photon absorber is a phthalocyanine dye, such as, but not limited to, IRDye®700DX (also known as "IR700"). Antibody-photoabsorber conjugates can be used for photoimmunotherapy.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Toxins can be employed with the monoclonal antibodies described herein to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, MO). Contemplated toxins also include variants of the toxins described herein (see, for example, see, U.S. Pat. Nos. 5,079,163 and 4,689,401). In one embodiment, the toxin is *Pseudomonas* exotoxin (PE) (U.S. Pat. No. 5,602,095). As used herein "*Pseudomonas* exotoxin" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., *J. Biol. Chem.* 264:14256-14261, 1989).

PE employed with the monoclonal antibodies described herein can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; U.S. Patent Application Publication No. 2015/0099707; PCT Publication Nos. WO 99/51643 and WO 2014/052064; Pai et al., *Proc. Natl. Acad. Sci. USA* 88:3358-3362, 1991; Kondo et al., *J. Biol. Chem.* 263:9470-9475, 1988; Pastan et al., *Biochim. Biophys. Acta* 1333:C1-C6, 1997.

Also contemplated herein are protease-resistant PE variants and PE variants with reduced immunogenicity, such as, but not limited to PE-LR, PE-6X, PE-8X, PE-LR/6X and PE-LR/8X (see, for example, Weldon et al., *Blood* 113(16): 3792-3800, 2009; Onda et al., *Proc Natl Acad Sci USA* 105(32):11311-11316, 2008; and PCT Publication Nos. WO 2007/016150, WO 2009/032954 and WO 2011/032022, which are herein incorporated by reference).

In some examples, the PE is a variant that is resistant to lysosomal degradation, such as PE-LR (Weldon et al., *Blood* 113(16):3792-3800, 2009; PCT Publication No. WO 2009/032954). In other examples, the PE is a variant designated PE-LR/6X (PCT Publication No. WO 2011/032022). In other examples, the PE variant is PE with reducing immunogenicity. In yet other examples, the PE is a variant designated PE-LR/8M (PCT Publication No. WO 2011/032022).

Modification of PE may occur in any previously described variant, including cytotoxic fragments of PE (for example, PE38, PE-LR and PE-LR/8M). Modified PEs may include any substitution(s), such as for one or more amino acid residues within one or more T-cell epitopes and/or B cell epitopes of PE, or deletion of one or more T-cell and/or B-cell epitopes (see, for example, U.S. Patent Application Publication No. 2015/0099707).

Contemplated forms of PE also include deimmunized forms of PE, for example versions with domain II deleted (for example, PE24). Deimmunized forms of PE are described in, for example, PCT Publication Nos. WO 2005/052006, WO 2007/016150, WO 2007/014743, WO 2007/031741, WO 2009/32954, WO 2011/32022, WO 2012/154530, and WO 2012/170617.

The antibodies described herein can also be used to target any number of different diagnostic or therapeutic compounds to cells expressing the tumor or viral antigen on their surface. Thus, an antibody of the present disclosure can be attached directly or via a linker to a drug that is to be delivered directly to cells expressing cell-surface antigen. This can be done for therapeutic, diagnostic or research purposes. Therapeutic agents include such compounds as nucleic acids, proteins, peptides, amino acids or derivatives, glycoproteins, radioisotopes, photon absorbers, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an antibody can be an encapsulation system, such as a nanoparticle, liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are well known to those of skill in the art (see, for example, U.S. Pat. No. 4,957,735; Connor et al., *Pharm. Ther.* 28:341-365, 1985).

Antibodies described herein can also be covalently or non-covalently linked to a detectable label. Detectable labels suitable for such use include any composition detectable by spectroscopic, photochemical, biochemical, immunochemical, electrical, optical or chemical means. Useful labels include magnetic beads, fluorescent dyes (for example, fluorescein isothiocyanate, Texas red, rhodamine, green fluorescent protein, and the like), radiolabels (for example, $^{3}H$, $^{125}I$, $^{35}S$, $^{14}C$, or $^{32}P$), enzymes (such as horseradish peroxidase, alkaline phosphatase and others commonly used in an ELISA), and colorimetric labels such as colloidal gold or colored glass or plastic (such as polystyrene, polypropylene, latex, and the like) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

VI. Antibody-Drug Conjugates (ADCs)

ADCs are compounds comprised of a tumor antigen-specific antibody (or antigen-binding fragment thereof) and a drug, typically a cytotoxic agent, such as an anti-microtubule agent or cross-linking agent. Because ADCs are capable of specifically targeting cancer cells, the drug can be much more potent than agents used for standard chemotherapy. The most common cytotoxic drugs currently used with ADCs have an $IC_{50}$ that is 100- to 1000-fold more potent than conventional chemotherapeutic agents. Common cytotoxic drugs include anti-microtubule agents, such as maytansinoids and auristatins (such as auristatin E and auristatin F). Other cytotoxins for use with ADCs include pyrrolobenzodiazepines (PDBs), which covalently bind the minor groove of DNA to form interstrand crosslinks. In many instances, ADCs comprise a 1:2 to 1:4 ratio of antibody to drug (Bander, *Clinical Advances in Hematology & Oncology* 10(8; suppl 10):3-7, 2012).

The antibody and drug can be linked by a cleavable or non-cleavable linker. However, in some instances, it is desirable to have a linker that is stable in the circulation to prevent systemic release of the cytotoxic drug that could result in significant off-target toxicity. Non-cleavable linkers prevent release of the cytotoxic agent before the ADC is internalized by the target cell. Once in the lysosome, digestion of the antibody by lysosomal proteases results in the release of the cytotoxic agent (Bander, *Clinical Advances in Hematology & Oncology* 10(8; suppl 10):3-7, 2012).

One method for site-specific and stable conjugation of a drug to a monoclonal antibody is via glycan engineering. Monoclonal antibodies have one conserved N-linked oligosaccharide chain at the Asn297 residue in the CH2 domain of each heavy chain (Qasba et al., *Biotechnol Prog* 24:520-526, 2008). Using a mutant β1,4-galactosyltransferase enzyme (Y289L-Gal-T1; U.S. Patent Application Publication Nos. 2007/0258986 and 2006/0084162, herein incorporated by reference), 2-keto-galactose is transferred to free GlcNAc residues on the antibody heavy chain to provide a chemical handle for conjugation.

The oligosaccharide chain attached to monoclonal antibodies can be classified into three groups based on the terminal galactose residues—fully galactosylated (two galactose residues; IgG-G2), one galactose residue (IgG-G1) or completely degalactosylated (IgG-G0). Treatment of a monoclonal antibody with β1,4-galactosidase converts the antibody to the IgG-G0 glycoform. The mutant β1,4-galactosyltransferase enzyme is capable of transferring 2-keto-galactose or 2-azido-galactose from their respective UDP derivatives to the GlcNAc residues on the IgG-G1 and IgG-G0 glycoforms. The chemical handle on the transferred sugar enables conjugation of a variety of molecules to the monoclonal antibody via the glycan residues (Qasba et al., *Biotechnol Prog* 24:520-526, 2008).

Provided herein are ADCs that include a drug (such as a cytotoxic agent) conjugated to a monoclonal antibody that binds (such as specifically binds) mesothelin. In some embodiments, the drug is a small molecule. In some examples, the drug is a cross-linking agent, an anti-microtubule agent and/or anti-mitotic agent, or any cytotoxic agent suitable for mediating killing of tumor cells. Exemplary cytotoxic agents include, but are not limited to, a PDB, an auristatin, a maytansinoid, dolastatin, calicheamicin, nemorubicin and its derivatives, PNU-159682, anthracycline, vinca alkaloid, taxane, trichothecene, CC1065, camptothecin, elinafide, a combretastain, a dolastatin, a duocarmycin, an enediyne, a geldanamycin, an indolinobenzodiazepine dimer, a puromycin, a tubulysin, a hemiasterlin, a spliceostatin, or a pladienolide, as well as stereoisomers, isosteres, analogs, and derivatives thereof that have cytotoxic activity.

In some embodiments, the ADC comprises a pyrrolobenzodiazepine (PBD). The natural product anthramycin (a PBD) was first reported in 1965 (Leimgruber et al., *J Am Chem Soc,* 87:5793-5795, 1965; Leimgruber et al., *J Am Chem Soc,* 87:5791-5793, 1965). Since then, a number of PBDs, both naturally-occurring and synthetic analogues, have been reported (Gerratana, *Med Res Rev* 32(2):254-293, 2012; and U.S. Pat. Nos. 6,884,799; 7,049,311; 7,067,511; 7,265,105; 7,511,032; 7,528,126; and 7,557,099). As one example, PDB dimers recognize and bind to specific DNA sequences, and have been shown to be useful as cytotoxic agents. PBD dimers have been conjugated to antibodies and the resulting ADC shown to have anti-cancer properties (see, for example, US 2010/0203007). Exemplary linkage sites on the PBD dimer include the five-membered pyrrolo ring, the tether between the PBD units, and the N10-C11 imine group (see WO 2009/016516; US 2009/304710; US 2010/047257; US 2009/036431; US 2011/0256157; and WO 2011/130598).

In some embodiments, the ADC comprises an antibody conjugated to one or more maytansinoid molecules. Maytansinoids are derivatives of maytansine, and are mitotic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

In some embodiments, the ADC includes an antibody conjugated to a dolastatin or auristatin, or an analog or derivative thereof (see U.S. Pat. Nos. 5,635,483; 5,780,588; 5,767,237; and 6,124,431). Auristatins are derivatives of the marine mollusk compound dolastatin-10. Dolastatins and auristatins have been shown to interfere with microtubule dynamics, GTP hydrolysis, and nuclear and cellular division (Woyke et al., *Antimicrob Agents and Chemother* 45(12): 3580-3584, 2001) and have anticancer (U.S. Pat. No. 5,663, 149) and antifungal activity (Pettit et al., *Antimicrob Agents Chemother* 42:2961-2965, 1998). Exemplary dolastatins and auristatins include, but are not limited to, dolastatin 10, auristatin E, auristatin F, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB), and other auristatins (see, for example, U.S. Publication No. 2013/0129753).

In some embodiments, the ADC comprises an antibody conjugated to one or more calicheamicin molecules. The calicheamicin family of antibiotics, and analogues thereof, are capable of producing double-stranded DNA breaks at sub-picomolar concentrations (Hinman et al., *Cancer Res* 53:3336-3342, 1993; Lode et al., *Cancer Res* 58:2925-2928, 1998). Exemplary methods for preparing ADCs with a calicheamicin drug moiety are described in U.S. Pat. Nos. 5,712,374; 5,714,586; 5,739,116; and 5,767,285.

In some embodiments, the ADC comprises an anthracycline. Anthracyclines are antibiotic compounds that exhibit cytotoxic activity. It is believed that anthracyclines can operate to kill cells by a number of different mechanisms, including intercalation of the drug molecules into the DNA of the cell thereby inhibiting DNA-dependent nucleic acid synthesis; inducing production of free radicals which then react with cellular macromolecules to cause damage to the cells; and/or interactions of the drug molecules with the cell membrane. Non-limiting exemplary anthracyclines include doxorubicin, epirubicin, idarubicin, daunomycin, daunorubicin, doxorubicin, epirubicin, nemorubicin, valrubicin and mitoxantrone, and derivatives thereof. For example, PNU-159682 is a potent metabolite (or derivative) of nemorubicin (Quintieri et al., *Clin Cancer Res* 11(4):1608-1617, 2005). Nemorubicin is a semisynthetic analog of doxorubicin with a 2-methoxymorpholino group on the glycoside amino of doxorubicin (Grandi et al., *Cancer Treat Rev* 17:133, 1990; Ripamonti et al., *Br J Cancer* 65:703-707, 1992).

In some embodiments, the ADC can further include a linker. In some examples, the linker is a bifunctional or multifunctional moiety that can be used to link one or more drug moieties to an antibody to form an ADC. In some embodiments, ADCs are prepared using a linker having reactive functionalities for covalently attaching to the drug and to the antibody. For example, a cysteine thiol of an antibody can form a bond with a reactive functional group of a linker or a drug-linker intermediate to make an ADC.

In some examples, a linker has a functionality that is capable of reacting with a free cysteine present on an antibody to form a covalent bond. Exemplary linkers with such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates.

In some examples, a linker has a functionality that is capable of reacting with an electrophilic group present on an antibody. Examples of such electrophilic groups include, but are not limited to, aldehyde and ketone carbonyl groups. In some cases, a heteroatom of the reactive functionality of the linker can react with an electrophilic group on an antibody and form a covalent bond to an antibody unit. Non-limiting examples include hydrazide, oxime, amino, hydrazine, thiosemicarbazone, hydrazine carboxylate and arylhydrazide.

In some examples, the linker is a cleavable linker, which facilitates release of the drug. Examples of cleavable linkers include acid-labile linkers (for example, comprising hydrazone), protease-sensitive linkers (for example, peptidase-sensitive), photolabile linkers, and disulfide-containing linkers (Chari et al., *Cancer Res* 52:127-131, 1992; U.S. Pat. No. 5,208,020).

The ADCs disclosed herein can be used for the treatment of a mesothelin-positive cancer alone or in combination with another therapeutic agent and/or in combination with any standard therapy for the treatment of cancer (such as surgical resection of the tumor, chemotherapy or radiation therapy).

VII. Multi-Specific Antibodies

Multi-specific antibodies are recombinant proteins comprised of two or more monoclonal antibodies (such as single-domain antibodies) or antigen-binding fragments of two or more different monoclonal antibodies. For example, bispecific antibodies are comprised of antigen-binding fragments of two different monoclonal antibodies (or two different single-domain antibodies). Thus, bispecific antibodies bind two different antigens and trispecific antibodies bind three different antigens. Multi-specific antibodies can be used for cancer immunotherapy by simultaneously targeting, for example, both CTLs (such as a CTL receptor component such as CD3) or effector natural killer (NK) cells, and at least one tumor antigen. The mesothelin-specific monoclonal antibodies disclosed herein can be used to generate multi-specific (such as bispecific or trispecific) antibodies that target both mesothelin and CTLs, or target both mesothelin and NK cells, thereby providing a means to treat mesothelin-expressing cancers. In one example, the mesothelin-specific monoclonal antibodies disclosed herein are used to generate multi-specific (such as bispecific or trispecific) antibodies that target both mesothelin and PD1, PDL1, EGFR, or VEGF, thereby providing a means to treat mesothelin-expressing cancers.

Provided herein are multi-specific, such as trispecific or bispecific, monoclonal antibodies comprising a mesothelin-specific monoclonal antibody. In some embodiments, the multi-specific monoclonal antibody further comprises a monoclonal antibody that specifically binds a component of the T cell receptor, such as CD3. In other embodiments, the multi-specific monoclonal antibody further comprises a monoclonal antibody that specifically binds a NK cell activating receptor, such as CD16, Ly49, or CD94. Also provided are isolated nucleic acid molecules and vectors encoding the multi-specific antibodies, and host cells comprising the nucleic acid molecules or vectors. Multi-specific antibodies comprising a mesothelin-specific antibody can be used for the treatment of cancers that express mesothelin. Thus, provided herein are methods of treating a subject with cancer by selecting a subject with a cancer that expresses mesothelin, and administering to the subject a therapeutically effective amount of the mesothelin-targeting multi-specific antibody.

VIII. Antibody-Nanoparticle Conjugates

The monoclonal antibodies disclosed herein can be conjugated to a variety of different types of nanoparticles to deliver cytotoxic agents or other anti-cancer agents directly to tumor cells via binding of the antibody to mesothelin expressed on the surface of tumor cells. The use of nanoparticles reduces off-target side effects and can also improve drug bioavailability and reduce the dose of a drug required to achieve a therapeutic effect. Nanoparticle formulations can be tailored to suit the drug that is to be carried or encapsulated within the nanoparticle. For example, hydrophobic molecules can be incorporated inside the core of a nanoparticle, while hydrophilic drugs can be carried within an aqueous core protected by a polymeric or lipid shell. Examples of nanoparticles include, but at not limited to, nanospheres, nanocapsules, liposomes, dendrimers, polymeric micelles, niosomes, and polymeric nanoparticles (Fay and Scott, Immunotherapy 3(3):381-394, 2011).

Liposomes are currently one of the most common types of nanoparticles used for drug delivery. An antibody conjugated to a liposome is often referred to as an "immunoliposome." The liposomal component of an immunoliposome is typically a lipid vesicle of one or more concentric phospholipid bilayers. In some cases, the phospholipids are composed of a hydrophilic head group and two hydrophobic chains to enable encapsulation of both hydrophobic and hydrophilic drugs. Conventional liposomes are rapidly removed from the circulation via macrophages of the reticuloendothelial system (RES). To generate long-circulating liposomes, the composition, size and charge of the liposome can be modulated. The surface of the liposome may also be modified, such as with a glycolipid or sialic acid. For example, the inclusion of polyethylene glycol (PEG) significantly increases circulation half-life. Liposomes for use as drug delivery agents, including for preparation of immunoliposomes, have been described in the art (see, for example, Paszko and Senge, *Curr Med Chem* 19(31)5239-5277, 2012; Immordino et al., *Int J Nanomedicine* 1(3):297-315, 2006; U.S. Patent Application Publication Nos. 2011/0268655; 2010/00329981).

Niosomes are non-ionic surfactant-based vesicles having a structure similar to liposomes. The membranes of niosomes are composed only of nonionic surfactants, such as polyglyceryl-alkyl ethers or N-palmitoylglucosamine. Niosomes range from small, unilamellar to large, multilamellar particles. These nanoparticles are monodisperse, water-soluble, chemically stable, have low toxicity, are biodegradable and non-immunogenic, and increase bioavailability of encapsulated drugs.

Dendrimers include a range of branched polymer complexes. These nanoparticles are water-soluble, biocompatible and are sufficiently non-immunogenic for human use. Generally, dendrimers consist of an initiator core, surrounded by a layer of a selected polymer that is grafted to the core, forming a branched macromolecular complex. Dendrimers are typically produced using polymers such as poly(amidoamine) or poly(L-lysine). Dendrimers have been used for a variety of therapeutic and diagnostic applications, including for the delivery of DNA, RNA, bioimaging contrast agents and chemotherapeutic agents.

Polymeric micelles are composed of aggregates of amphiphilic co-polymers (consisting of both hydrophilic and hydrophobic monomer units) assembled into hydrophobic cores, surrounded by a corona of hydrophilic polymeric chains exposed to the aqueous environment. In many cases, the polymers used to prepare polymeric micelles are heterobifunctional copolymers composed of a hydrophilic block of PEG, poly(vinyl pyrrolidone) and hydrophobic poly(L-lactide) or poly(L-lysine) that forms the particle core. Polymeric micelles can be used to carry drugs that have poor solubility. These nanoparticles have been used to encapsulate a number of anti-cancer drugs, including doxorubicin and camptothecin. Cationic micelles have also been developed to carry DNA or RNA molecules.

Polymeric nanoparticles include both nanospheres and nanocapsules. Nanospheres consist of a solid matrix of polymer, while nanocapsules contain an aqueous core. The formulation selected typically depends on the solubility of the therapeutic agent to be carried/encapsulated; poorly water-soluble drugs are more readily encapsulated within a nanospheres, while water-soluble and labile drugs, such as DNA and proteins, are more readily encapsulated within nanocapsules. The polymers used to produce these nanoparticles include, for example, poly(acrylamide), poly(ester), poly(alkylcyanoacrylates), poly(lactic acid) (PLA), poly(glycolic acids) (PGA), and poly(D,L-lactic-co-glycolic acid) (PLGA).

Antibodies (or fragments thereof) can be conjugated to a suitable nanoparticle according to standard methods known in the art. For example, conjugation can be either covalent or non-covalent. In some embodiments in which the nanoparticle is a liposome, the antibody is attached to a sterically stabilized, long circulation liposome via a PEG chain. Coupling of antibodies or antibody fragments to a liposome can also involve thioester bonds, for example by reaction of thiols and maleimide groups. Cross-linking agents can be used to create sulfhydryl groups for attachment of antibodies to nanoparticles (Paszko and Senge, *Curr Med Chem* 19(31) 5239-5277, 2012).

IX. Compositions and Methods of Use

Compositions are provided that include one or more of the disclosed monoclonal antibodies that bind (for example specifically bind) mesothelin in a carrier. Compositions comprising ADCs, CARs (and CTLs comprising CARs), multi-specific (such as bispecific or trispecific) antibodies, antibody-nanoparticle conjugates, immunoliposomes and immunoconjugates are also provided. The compositions can be prepared in unit dosage forms for administration to a subject. The amount and timing of administration are at the discretion of the treating clinician to achieve the desired outcome. The antibody, ADC, CAR, CTL, multi-specific antibody, antibody-nanoparticle conjugate, immunoliposome or immunoconjugate can be formulated for systemic or local (such as intra-tumor) administration. In one example, the antibody is formulated for parenteral administration, such as intravenous administration.

The compositions for administration can include a solution of the antibody, ADC, CAR, CTL, multi-specific (such as bispecific or trispecific) antibody, antibody-nanoparticle conjugate, immunoliposome or immunoconjugate in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody (or ADC, CAR, multi-specific antibody, antibody-nanoparticle conjugate, or immunoconjugate) per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19th ed., Mack Publishing Company, Easton, PA (1995).

The single-domain antibodies disclosed herein can also be administered by other routes, including via inhalation, oral, topical or intraocular. In some examples, the single-domain antibody (or conjugate thereof) is administered via fine-needle.

Antibodies (or other therapeutic molecules) may be provided in lyophilized form and rehydrated with sterile water before administration, although they are also provided in sterile solutions of known concentration. The antibody solution is then added to an infusion bag containing 0.9% sodium chloride, USP, and in some cases administered at a dosage of from 0.5 to 15 mg/kg of body weight. Considerable experience is available in the art in the administration of antibody drugs, which have been marketed in the U.S. since the approval of RITUXAN™ in 1997. Antibodies, ADCs, CARs, multi-specific (such as bispecific or trispecific) antibodies, antibody-nanoparticle conjugates, immunoliposomes or immunoconjugates can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30-minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, PA, (1995). Particulate systems include, for example, microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., *Colloidal Drug Delivery Systems*, J. Kreuter, ed., Marcel Dekker, Inc., New York, NY, pp. 219-342 (1994); and Tice & Tabibi, *Treatise on Controlled Drug Delivery*, A. Kydonieus, ed., Marcel Dekker, Inc. New York, NY, pp. 315-339, (1992).

Polymers can be used for ion-controlled release of the antibody-based compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, PA (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

A. Therapeutic Methods

The antibodies, compositions, CARs (and CTLs expressing CARs), ADCs, multi-specific (such as bispecific or trispecific) antibodies, antibody-nanoparticle conjugates, immunoliposomes and immunoconjugates disclosed herein can be administered to slow or inhibit the growth of tumor cells or inhibit the metastasis of tumor cells, such as mesothelin-positive cancers. In these applications, a therapeutically effective amount of a composition is administered to a subject in an amount sufficient to inhibit growth, replication or metastasis of cancer cells, or to inhibit a sign or a symptom of the cancer. Suitable subjects may include those diagnosed with a cancer that expresses mesothelin, such as, but not limited to mesothelioma, prostate cancer, lung cancer, stomach cancer, squamous cell carcinoma, pancreatic cancer, cholangiocarcinoma, breast cancer (such as triple negative breast cancer) or ovarian cancer.

Provided herein is a method of treating a mesothelin-positive cancer in a subject by administering to the subject a therapeutically effective amount of a mesothelin-specific antibody, immunoconjugate, CAR (or CTLs expressing a CAR), ADC, multi-specific (such as bispecific or trispecific) antibody, antibody-nanoparticle conjugate, immunoliposome or composition disclosed herein. Also provided herein is a method of inhibiting tumor growth or metastasis of a mesothelin-positive cancer in a subject by administering to the subject a therapeutically effective amount of a mesothelin-specific antibody, immunoconjugate, CAR (such as a CTL expressing a CAR), ADC, multi-specific (such as bispecific or trispecific) antibody, antibody-nanoparticle conjugate, immunoliposome or composition disclosed herein. In some embodiments, the mesothelin-positive cancer is a mesothelioma, prostate cancer, lung cancer, stomach cancer, squamous cell carcinoma, pancreatic cancer, cholangiocarcinoma, breast cancer (such as triple negative breast cancer) or ovarian cancer. In some examples, the method reduces the volume of tumor (such as a metastasis) by at least 10%, at least 20%, at least 50%, at least 75%, at least 80%, at least 90%, at least 95%, or even 100%, for example as compared to a volume prior to treatment. In some examples, the method reduces the size of tumor (such as a metastasis) by at least 10%, at least 20%, at least 50%, at least 75%, at least 80%, at least 90%, at least 95%, or even 100%, for example as compared to a size prior to treatment, In some examples, the method reduces the number of metastases at least 10%, at least 20%, at least 50%, at least 75%, at least 80%, at least 90%, at least 95%, or even 100%, for example as compared to a number prior to treatment, In some examples, the method increases the prognosis of a subject, such as increases the lifespan of the subject by at least 4 months, at least 6 months, at least 8 months, at least 9 months, at least 12 months, at least 24 months, at least 36 months, or at least 60 months, for example as compared to a number prior to treatment, In some examples, combinations of these effects are achieved.

A therapeutically effective amount of a mesothelin-specific monoclonal antibody, ADC, CAR (for example a CTL expressing a CAR), multi-specific (such as bispecific or trispecific) antibody, immunoconjugate, immunoliposome or composition disclosed herein will depend upon the severity of the disease, the type of disease, and the general state of the patient's health. A therapeutically effective amount of the antibody-based composition is that which provides either subjective relief of a symptom(s) or an objectively identifiable improvement as noted by the clinician or other qualified observer.

Administration of the mesothelin-specific antibodies, ADCs, CARs, immunoconjugates, multi-specific antibodies, antibody-nanoparticle conjugates, immunoliposomes and compositions disclosed herein can also be accompanied by administration of other anti-cancer agents or therapeutic treatments (such as surgical resection of a tumor). Any suitable anti-cancer agent can be administered in combination with the antibodies, compositions and immunoconjugates disclosed herein. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and other antibodies that specifically target cancer cells (such as anti-PD1, anti-PDL1, anti-VEGF, and anti-EGFR antibodies).

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include *vinca* alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

B. Methods for Diagnosis and Detection

Methods are provided herein for detecting mesothelin protein in vitro or in vivo. For example, the disclosed monoclonal antibodies can be used for in vivo tumor imaging. To use the disclosed antibodies as diagnostic reagents in vivo, the antibodies are labelled with a detectable moiety, such as a radioisotope, fluorescent label or positron emitting radionuclides. As one example, the single-domain antibodies disclosed herein can be conjugated to a positron emitting radionuclide for use in positron emission tomography (PET); this diagnostic process is often referred to as immunoPET. While full length antibodies can make good immunoPET agents, their biological half-life can require waiting several days prior to imaging, which increases associated non-target radiation doses. Smaller, single domain antibodies have biological half-lives amenable to same day imaging.

In other instances, mesothelin expression is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a human or non-human primate.

Provided herein is a method of determining if a subject has a mesothelin-positive cancer by contacting a sample from the subject with a mesothelin-specific monoclonal antibody disclosed herein; and detecting binding of the antibody to the sample. An increase in binding of the antibody to the sample as compared to binding of the antibody to a control sample identifies the subject as having a mesothelin-positive cancer.

In another embodiment, provided is a method of confirming a diagnosis of a mesothelin-positive cancer in a subject by contacting a sample from a subject diagnosed with a mesothelin-positive cancer with a mesothelin-specific monoclonal antibody disclosed herein; and detecting binding of the antibody to the sample. An increase in binding of the antibody to the sample as compared to binding of the antibody to a control sample confirms the diagnosis of a mesothelin-positive cancer in the subject.

In some examples of the disclosed methods, the monoclonal antibody is directly labeled.

In other examples, the methods further include contacting a second antibody (a detection antibody) that specifically binds the monoclonal antibody with the sample; and detecting the binding of the second antibody. An increase in binding of the second antibody to the sample as compared to binding of the second antibody to a control sample detects a mesothelin-positive cancer in the subject or confirms the diagnosis of a mesothelin-positive cancer in the subject.

In some cases, the cancer is a mesothelioma, prostate cancer, lung cancer, stomach cancer, squamous cell carcinoma, pancreatic cancer, cholangiocarcinoma, breast cancer (such as triple negative breast cancer) or ovarian cancer.

In some examples, the control sample is a sample from a subject without cancer. In particular examples, the sample is a blood or tissue sample.

In some embodiments of the methods of diagnosis and detection, the antibody that binds (for example specifically binds) mesothelin is directly labeled with a detectable label. In another embodiment, the antibody that binds (for example, specifically binds) mesothelin (the first antibody) is unlabeled and a second antibody or other molecule that can bind the antibody that specifically binds mesothelin is labeled. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

In an alternative embodiment, mesothelin can be assayed in a biological sample by a competition immunoassay utilizing mesothelin protein standards labeled with a detectable substance and an unlabeled antibody that specifically binds mesothelin. In this assay, the biological sample, the labeled mesothelin protein standards and the antibody that specifically bind mesothelin are combined and the amount of labeled mesothelin protein standard bound to the unlabeled antibody is determined. The amount of mesothelin in the biological sample is inversely proportional to the amount of labeled mesothelin protein standard bound to the antibody that specifically binds mesothelin.

The immunoassays and methods disclosed herein can be used for a number of purposes. In one embodiment, the antibody that specifically binds may be used to detect the production of mesothelin in cells in cell culture. In another embodiment, the antibody can be used to detect the amount of mesothelin in a biological sample, such as a tissue sample, or a blood or serum sample. In some examples, the mesothelin is cell-surface mesothelin. In other examples, the mesothelin protein is soluble (for example, in a cell culture supernatant or in a body fluid sample, such as a blood or serum sample).

In one embodiment, a kit is provided for detecting mesothelin in a biological sample, such as a blood sample or tissue sample. For example, to confirm a cancer diagnosis in a subject, a biopsy can be performed to obtain a tissue sample for histological examination. Kits for detecting mesothelin will typically comprise a monoclonal antibody that specifically binds mesothelin, such as any of the monoclonal antibodies disclosed herein, and can further include a labeled secondary antibody that can specifically bind to the anti-mesothelin antibody. In a specific embodiment, the anti-mesothelin antibody in the kit itself is labeled (for example, with a fluorescent, radioactive, or an enzymatic label).

In one embodiment, a kit includes instructional materials disclosing means of use of an antibody that binds mesothelin. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method.

In one embodiment, the diagnostic kit comprises an immunoassay. Although the details of the immunoassays may vary with the particular format employed, the method of detecting mesothelin in a biological sample generally includes the steps of contacting the biological sample with an antibody which specifically reacts, under immunologically reactive conditions, to mesothelin. The antibody is allowed to specifically bind under immunologically reactive conditions to form an immune complex, and the presence of the immune complex (bound antibody) is detected directly or indirectly.

The antibodies disclosed herein can also be utilized in immunoassays, such as, but not limited to radioimmunoassays (RIAs), ELISA, or immunohistochemical assays. The antibodies can also be used for fluorescence activated cell sorting (FACS). FACS employs a plurality of color channels, low angle and obtuse light-scattering detection channels, and impedance channels, among other more sophisticated levels of detection, to separate or sort cells (see U.S. Pat. No. 5,061,620). Any of the monoclonal antibodies that bind mesothelin, as disclosed herein, can be used in these assays. Thus, the antibodies can be used in a conventional immunoassay, including, without limitation, an ELISA, an RIA, FACS, tissue immunohistochemistry, Western blot or immunoprecipitation.

The following examples are provided to illustrate certain particular features and/or embodiments. These examples should not be construed to limit the disclosure to the particular features or embodiments described.

EXAMPLES

Example 1: Camel VHH Antibodies that Bind Human and Mouse Mesothelin

This example describes the identification and characterization of A101 and G8, two camel (*Camelus dromedaries*) single domain (VHH) monoclonal antibodies that bind both human and mouse mesothelin with high affinity.

Figure 2:
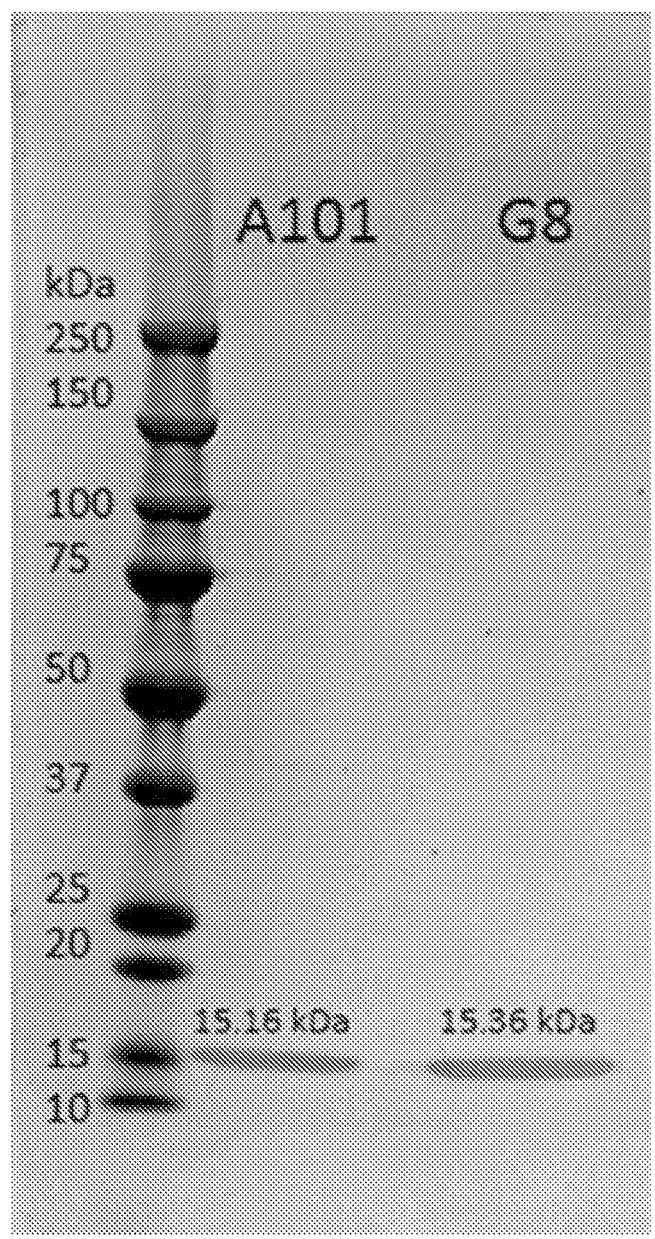
FIG. 2: SDS page showing purity and molecular weight of A101 and G8. A101 is 15.16 kDa and G8 is 15.36 kDa.

Antibodies A101 and G8 were isolated from a camel VHH phage display library by sequential panning. A polyclonal phage ELISA was performed to assess binding of phage clones to human and mouse mesothelin after each of four rounds of panning. After four rounds, phage clones demonstrated strong binding to both human and mouse mesothelin (FIG. 1). VHH clones A101 and G8 were isolated from the phage library and further characterized. The purity and molecular weight of A101 and G8 are shown in FIG. 2. The nucleotide and amino acid sequences of A101 are set forth herein as SEQ ID NO: 1 and SEQ ID NO: 2, respectively. The nucleotide and amino acid sequences of G8 are set forth herein as SEQ ID NO: 3 and SEQ ID NO: 4, respectively.

Figure 3:
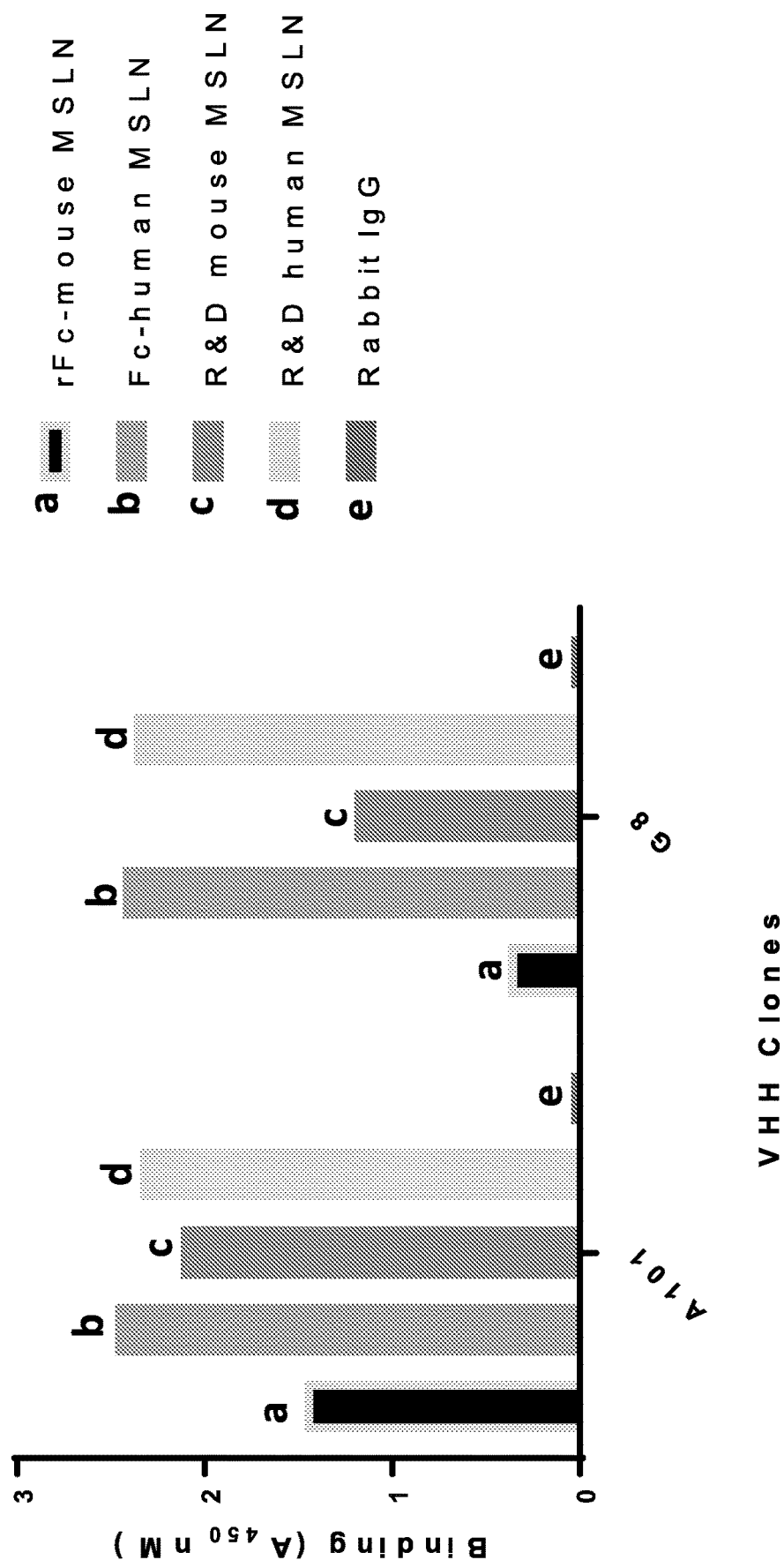
FIG. 3: ELISA analysis of A101 and G8 anti-mesothelin VHH antibody to human and mouse mesothelin proteins.

The A101 and G8 antibodies were assessed for binding to human and mouse mesothelin by ELISA (FIG. 3). R&D mesothelin is a monomer with a His tag and has no Fc. Fc-mesothelin is a bivalent rabbit Fc fusion protein. As shown in FIG. 3, the A101 and G8 antibodies bound both human and mouse mesothelin proteins.

Figure 4:
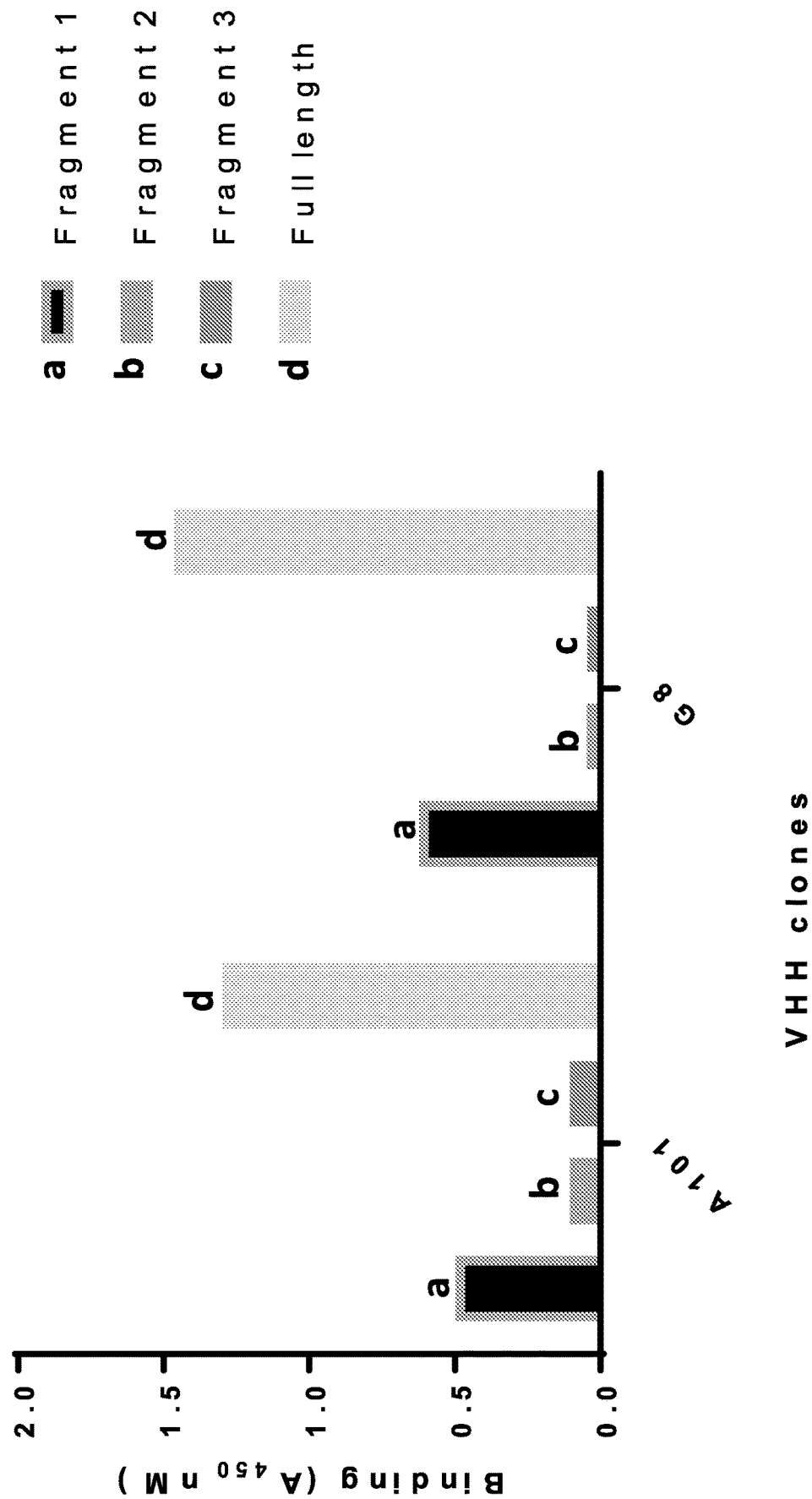
FIG. 4: ELISA analysis of A101 and G8 anti-mesothelin VHH antibody to fragments of mesothelin to determine epitope binding. Both antibodies bound mesothelin fragment 1 and full-length mesothelin.
Figure 5A:
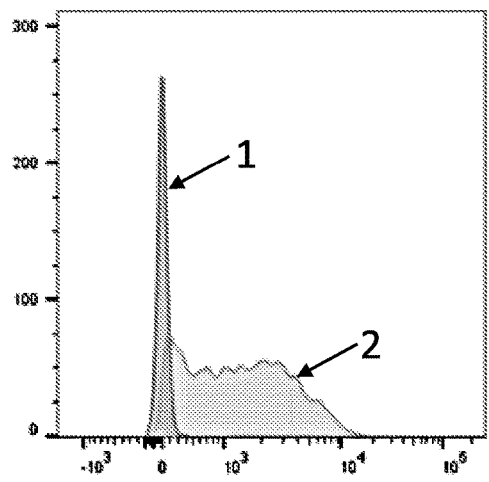
FIGS. 5A-5C: Flow cytometry analysis of cell surface mesothelin expression using the A101 antibody.
Figure 5A:
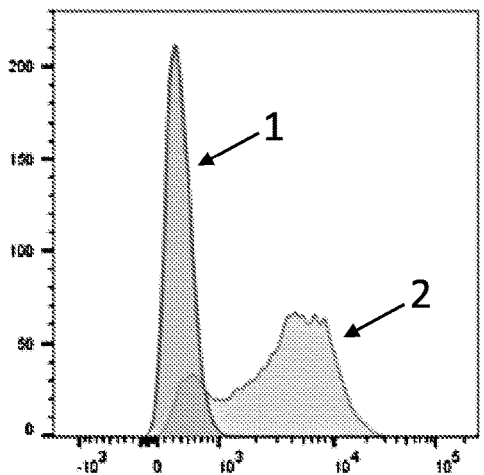
Figure 5A:
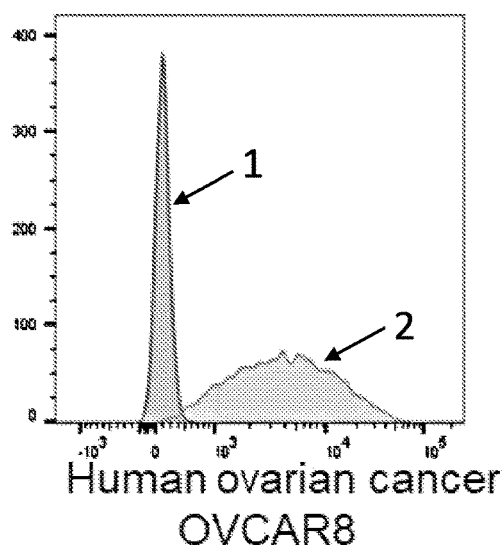
Figure 5A:
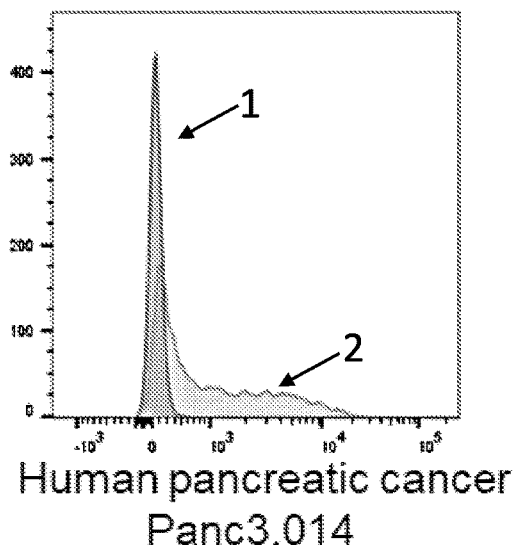
Figure 5B:
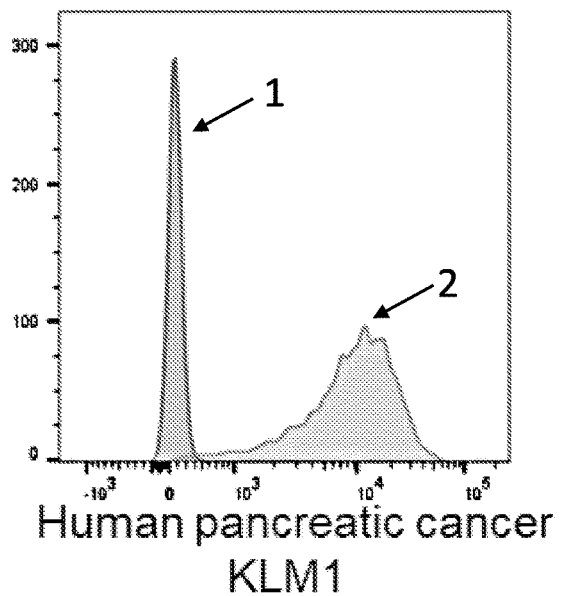
Figure 5B:
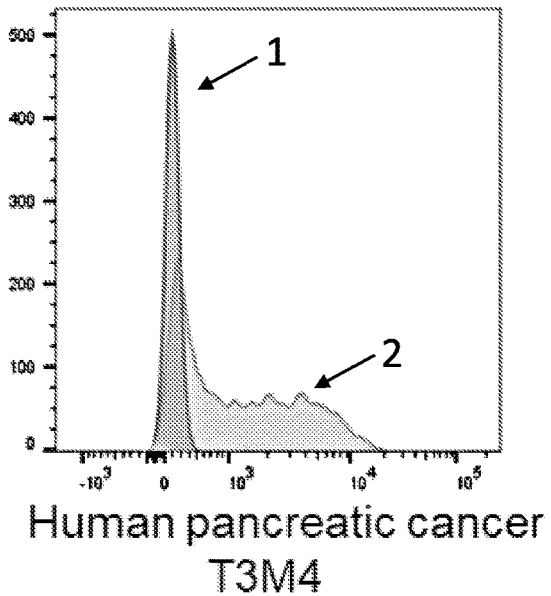
Figure 5B:
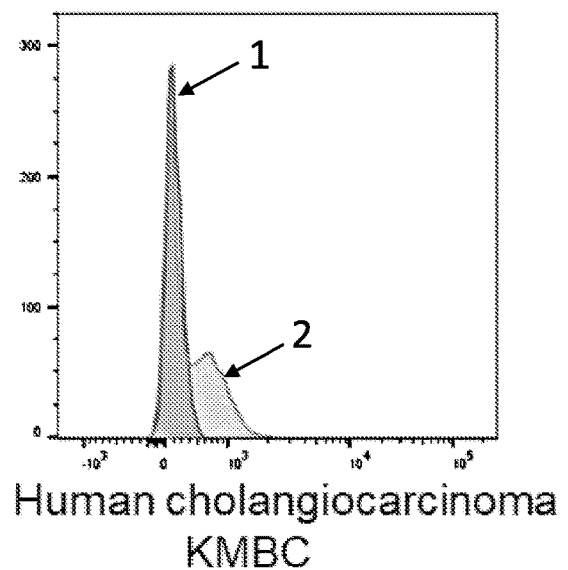
Figure 5B:
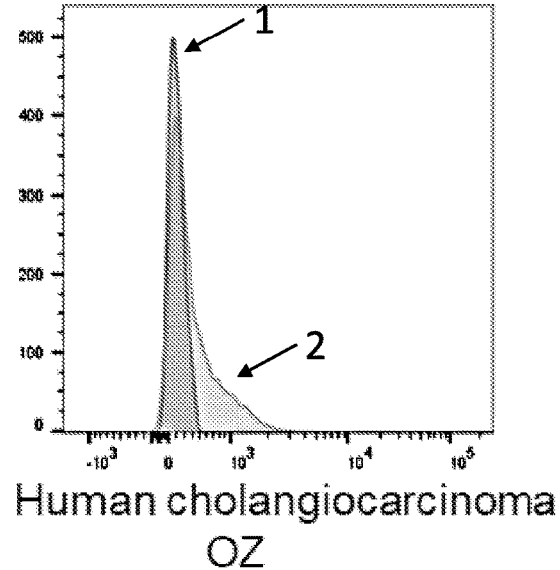
Figure 5C:
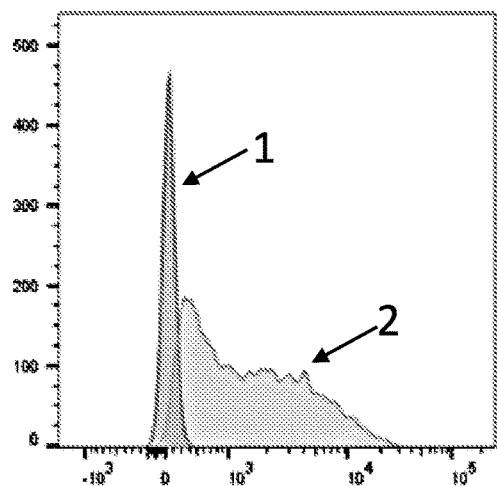
Figure 5C:
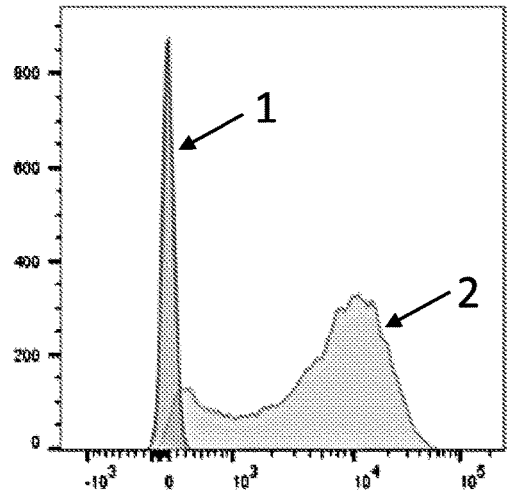
Figure 5C:
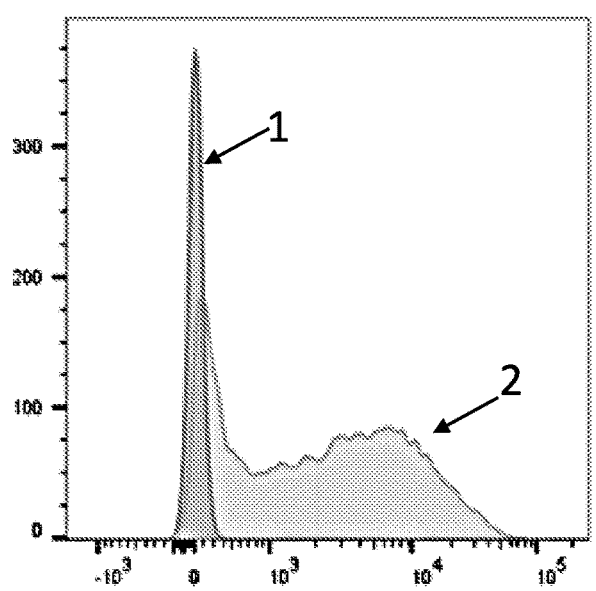
Figure 6A:
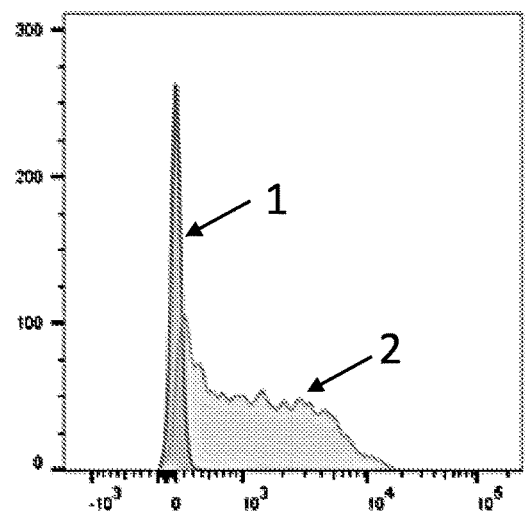
Figure 6A:
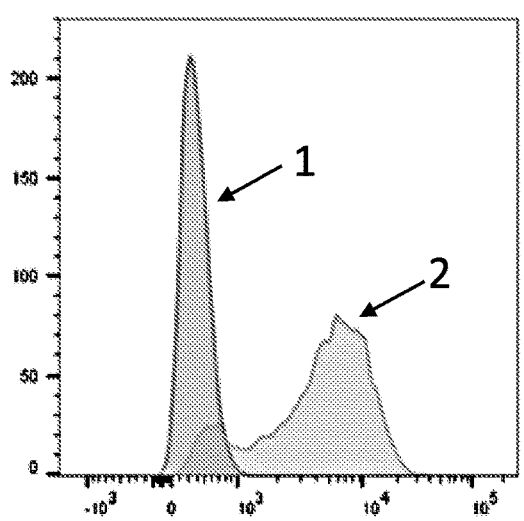
Figure 6A:
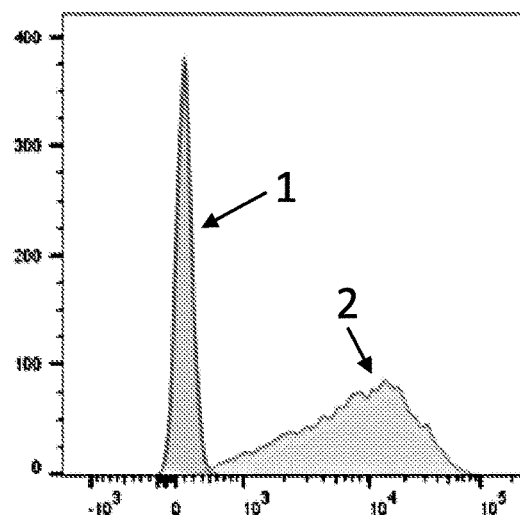
Figure 6A:
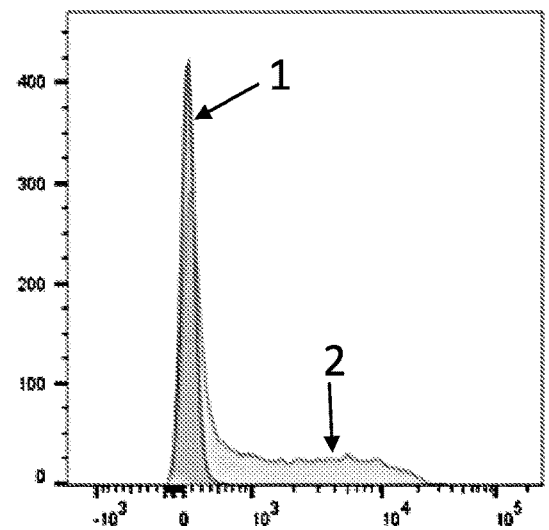
Figure 6B:
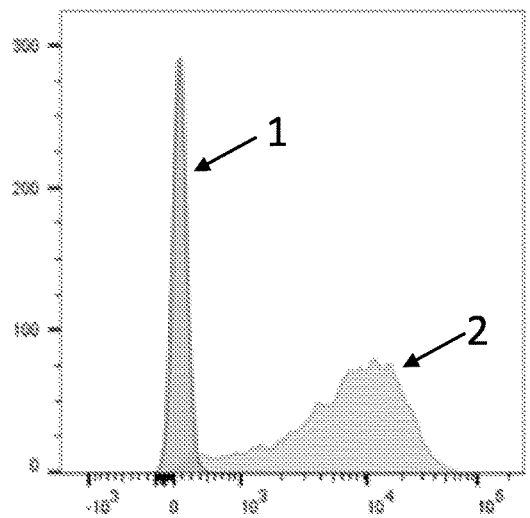
Figure 6B:
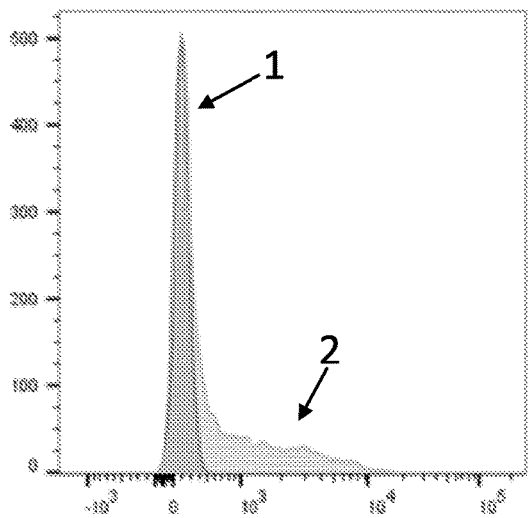
Figure 6B:
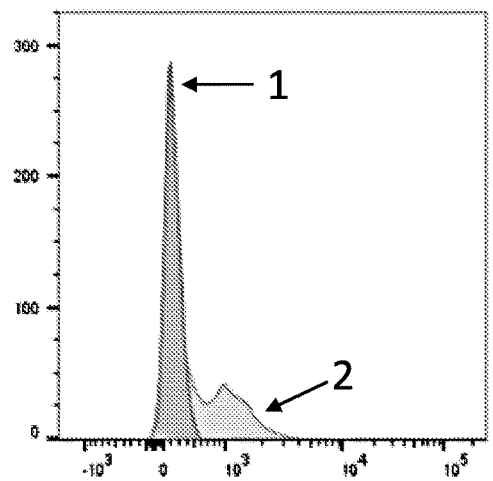
Figure 6B:
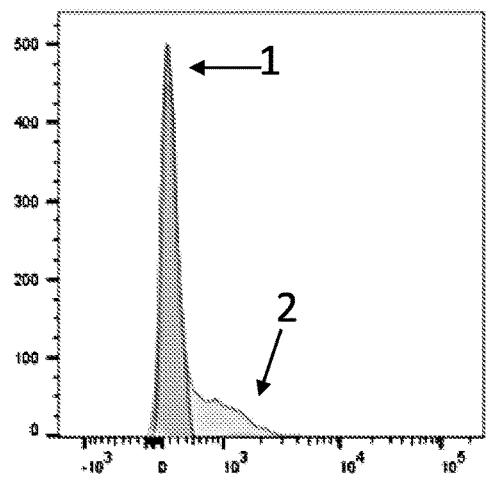

To determine what epitope(s) of mesothelin that A101 and G8 bind, a competitive ELISA was performed using either full-length human mesothelin protein, or fragments of mesothelin: Fragment 1 (residues 296-390), Fragment 2 (residues 391-486) and Fragment 3 (residues 487-598), numbering based on human mesothelin having the amino acid sequence of SEQ ID NO: 12 (see Kaneko et al., *J Biol Chem* 284(6): 3739-3749, 2009). The results demonstrated that A101 and G8 both bound Fragment 1 and full-length mesothelin, indicating that the epitope for each antibody is found in the N-terminal fragment 1 (FIG. 4).

Figure 11:
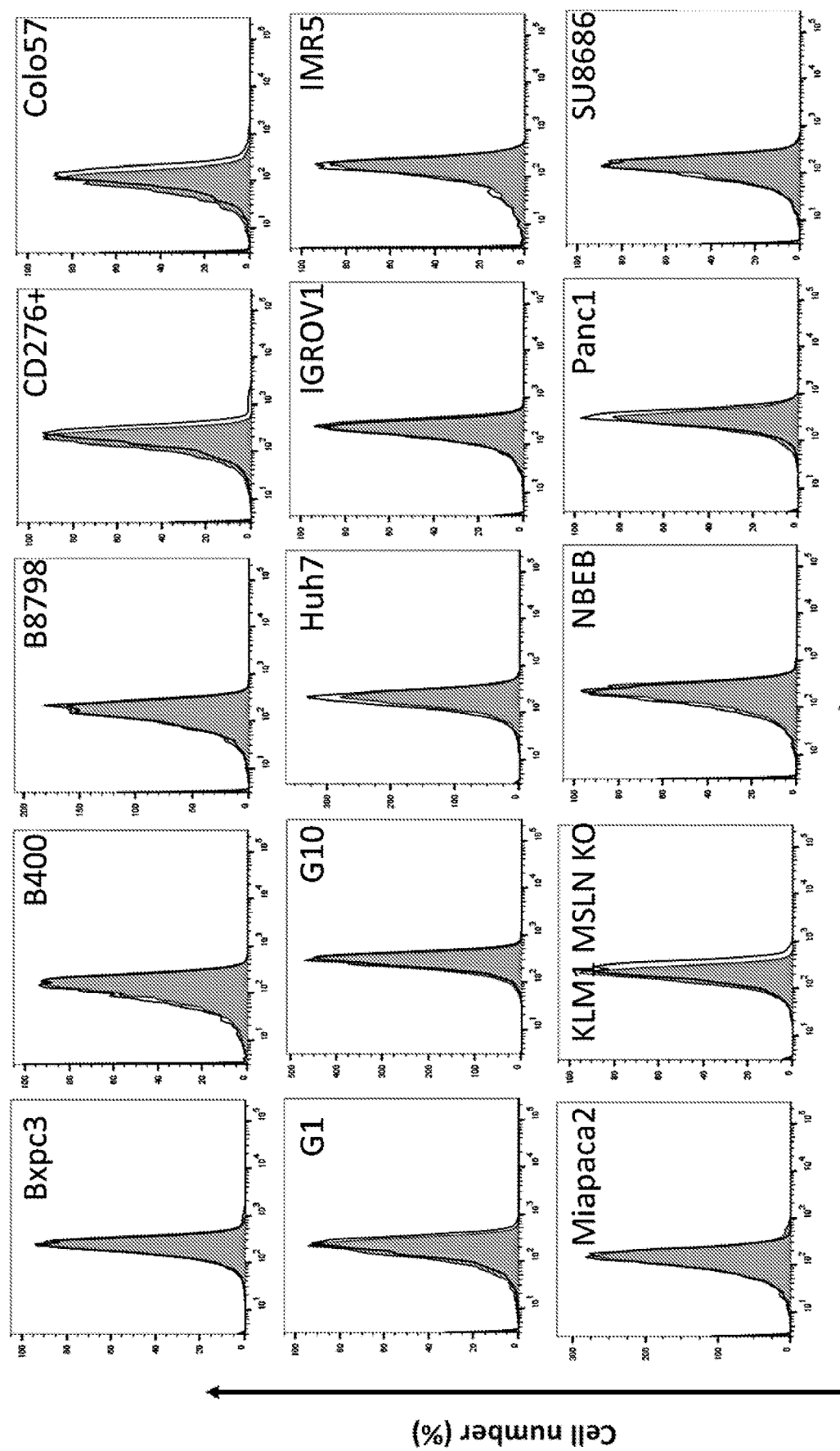
FIG. 11: The A101 camel antibody does not bind mesothelin-negative cells lines. No binding was detected for A101 (5 µg/ml) on mesothelin-negative cell lines, indicating A101 specifically binds mesothelin.
Figure 12:
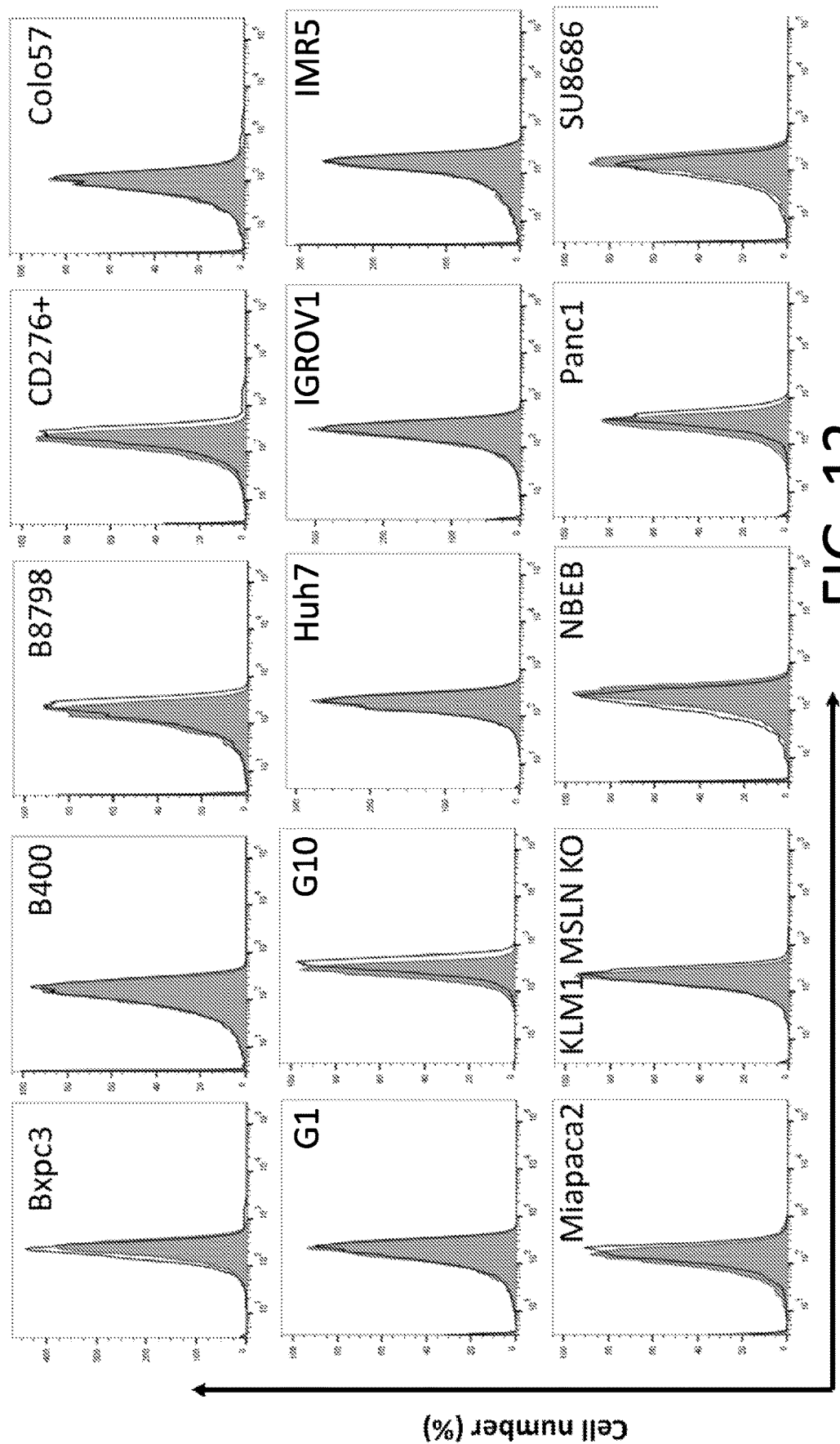
FIG. 12: The G8 camel antibody does not bind mesothelin-negative cells lines. No binding was detected for G8 (5 µg/ml) on mesothelin-negative cell lines, indicating G8 specifically binds mesothelin.

Binding of A101 (FIGS. 5A-5C) and G8 (FIGS. 6A-6C) to cell-surface expressed mesothelin was evaluated by flow cytometry. The binding experiments included human mesothelioma cancer cell lines M30 and H226, human ovarian cancer cell line OVCAR8, human pancreatic cell lines Panc3.014, KLM1 and T3M4, human cholangiocarcinoma cancer cell lines KMBC and OZ, and mouse pancreatic cancer cell lines PDA95775, CREP133234 and CREP133239. Cells were contacted with 10 µg/ml A101 or G8 and antibody binding to the cell surface was determined by flow cytometry. As shown in FIGS. 5A-5C and 6A-6C, both antibodies were able to bind mesothelin on the surface of all cell lines tested. Neither of the antibodies were able to bind mesothelin-negative cells lines (FIG. 11 and FIG. 12).

Figure 7A:
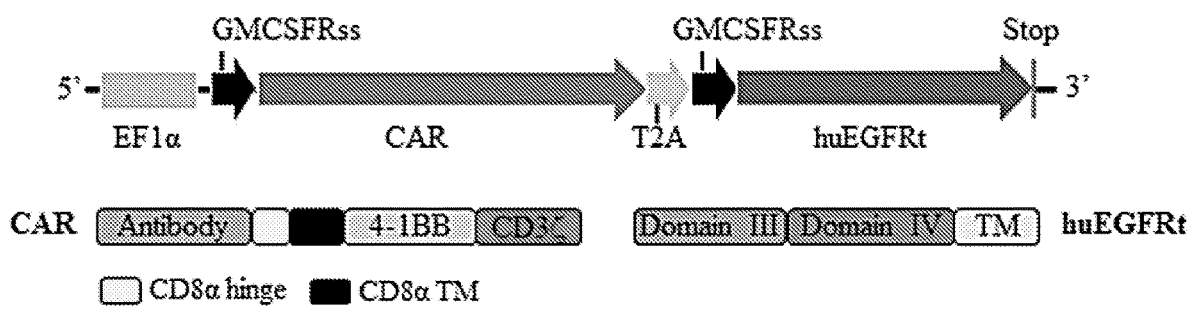
FIGS. 7A-7B: Generation of mesothelin-targeted CAR T cells.
Figure 7B:
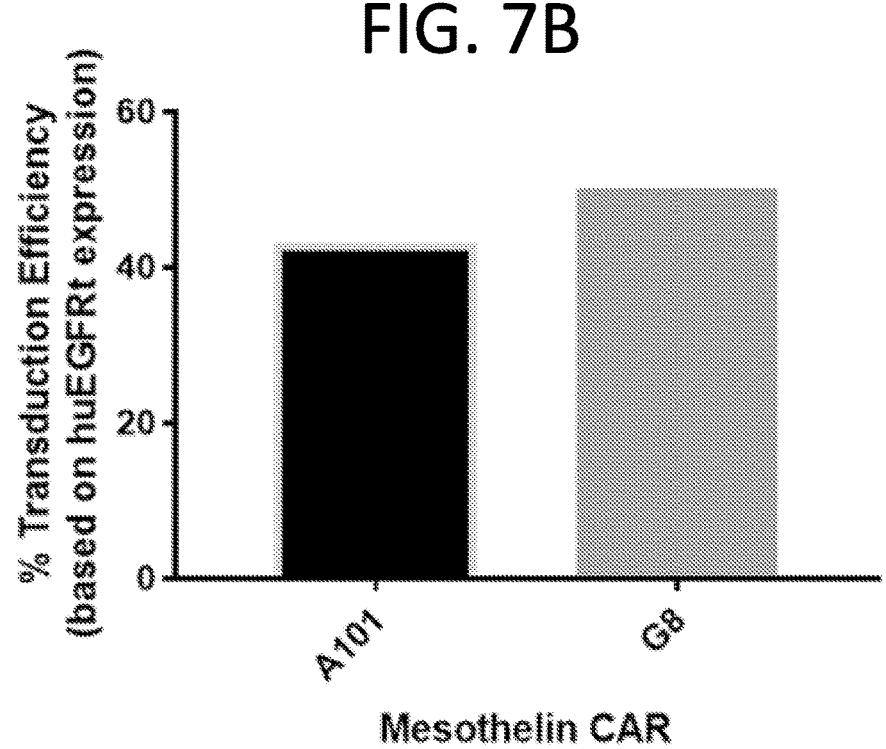

A101 and G8 were used to generate mesothelin-targeted CAR T cells. Lentiviral constructs expressing a CAR comprising VHH antibody A101 or VHH antibody G8 along with truncated human EGFR (huEGFRt) were produced (FIG. 7A; see also Section IV above). To confirm successful transduction of the vectors and expression of the CARs in T cells, flow cytometry was used to detect huEGFRt expression. As shown in FIG. 7B, transduction efficiency was approximately 40-50%.

Figure 8:
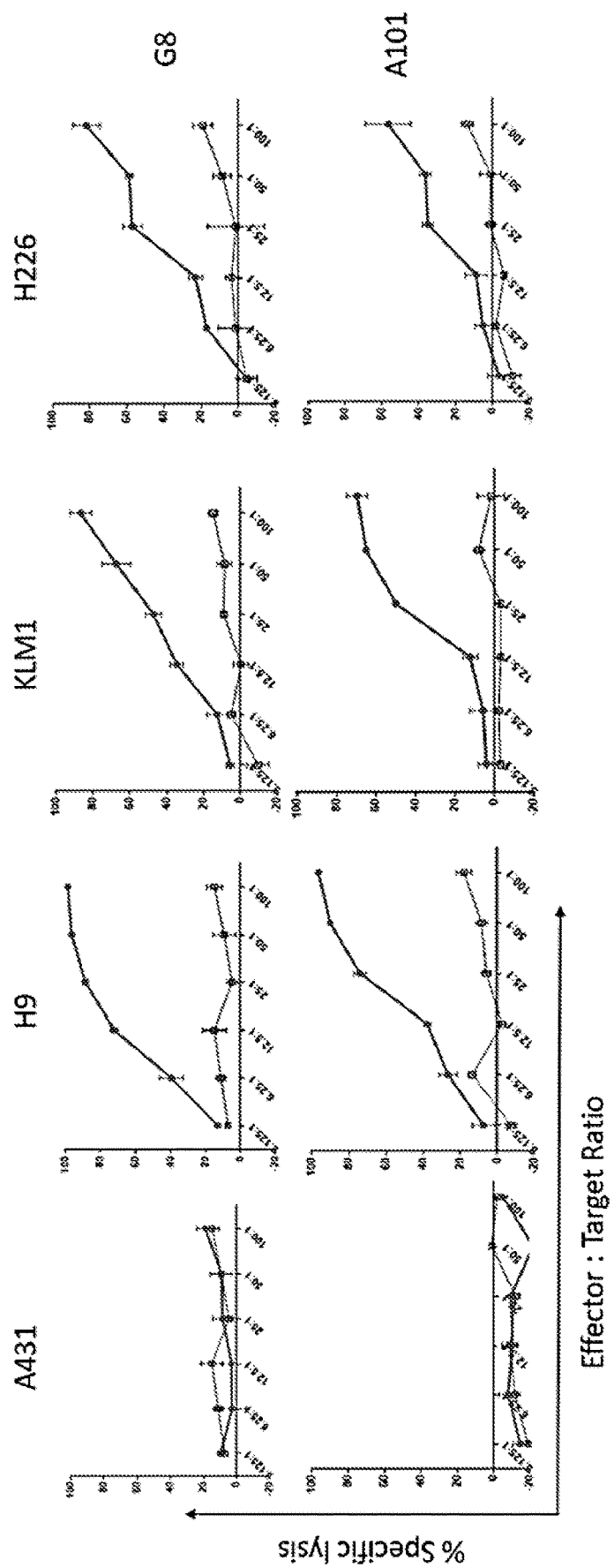
FIG. 8: Killing of mesothelin-positive cells by T cells expressing CARs based on A101 or G8. Luciferase expressing A431 (mesothelin-negative), H9 (mesothelin overexpressed), KLM1 (pancreatic cancer), and H226 (mesothelioma) cells were co-cultured with mock (grey lines), A101 or G8 CAR-transduced T cells (blue lines) at the indicated E:T ratios for 20 hours, and specific lysis was measured using a luminescent-based cytolytic assay.

Mesothelin-positive cell killing by CAR T cells based on A101 or G8 was evaluated using the luciferase expressing A431 (mesothelin negative), H9 (mesothelin overexpressed), KLM1 (pancreatic cancer), and H226 (mesothelioma) cells. Cells were co-cultured with A101 or G8 CAR-transduced T cells at E:T ratios ranging from 3.125:1 to 100:1 for 20 hours, and specific lysis was measured using a luminescent-based cytolytic assay. As shown in FIG. 8, mesothelin-targeted CAR T cells induced specific lysis of all mesothelin-expressing cells (H9, KLM1 and H226), but not mesothelin-negative A431 cells.

Figure 9A:
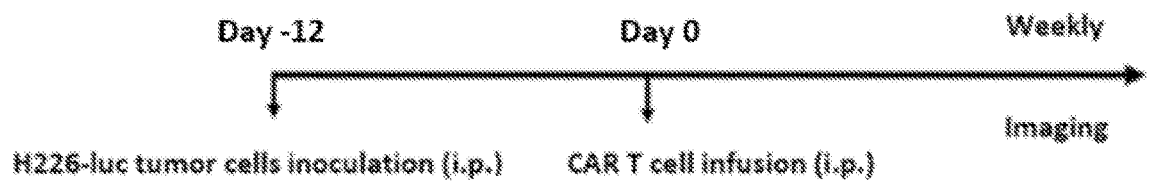
FIGS. 9A-9C: Mesothelin-targeted CAR T cells demonstrate potent activity in mice bearing human mesothelioma tumors.
Figure 9B:
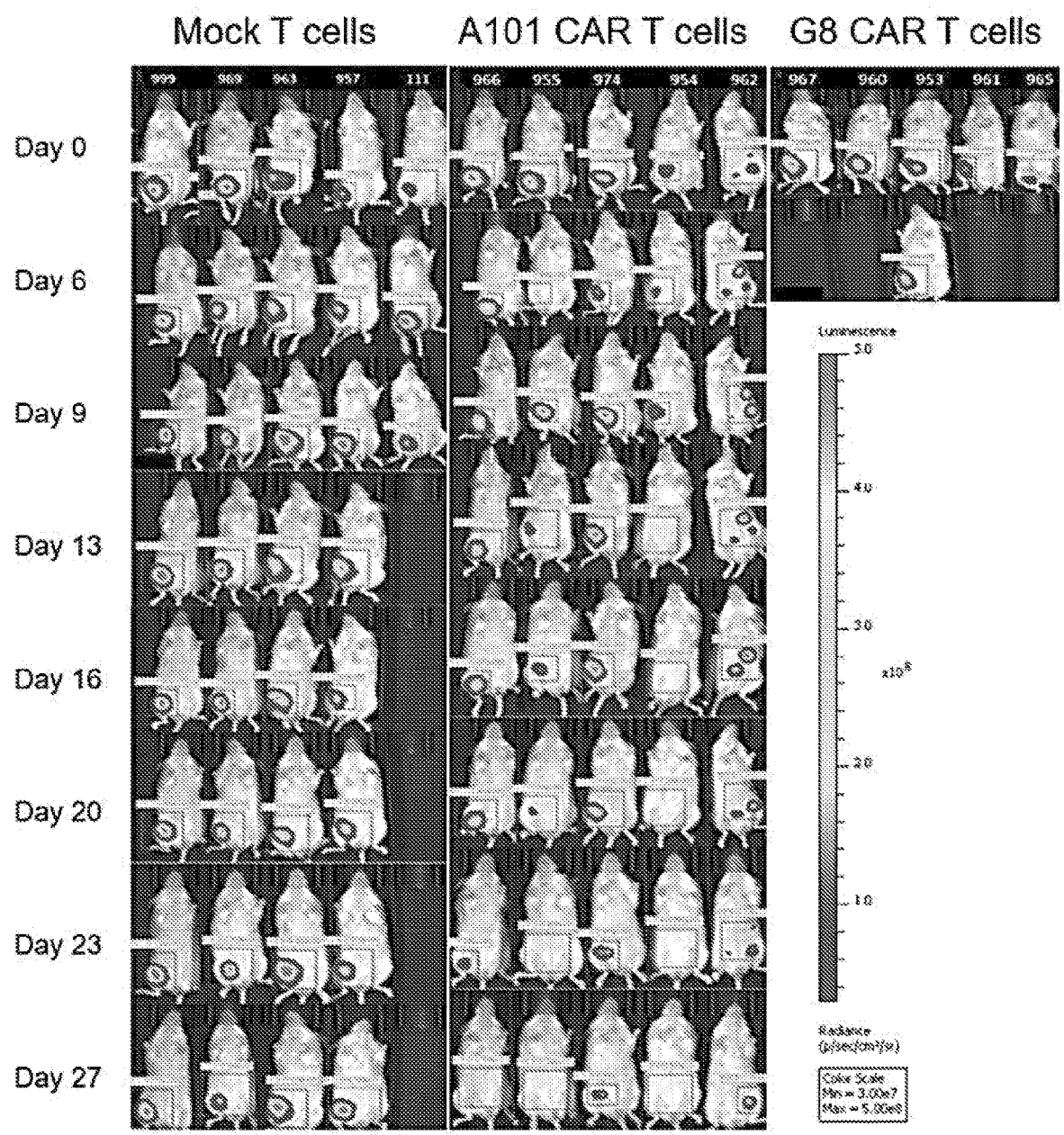
Figure 9C:
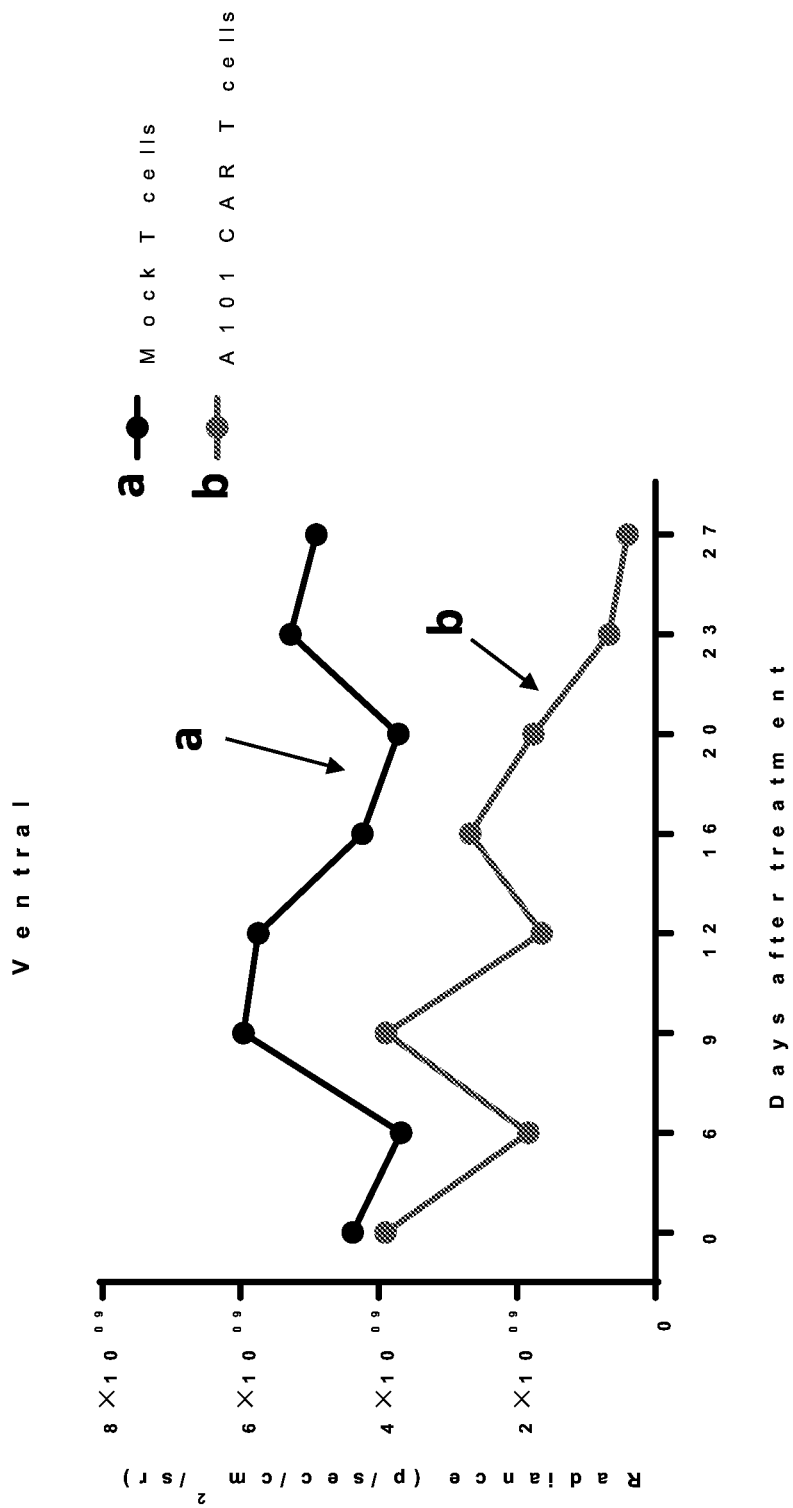

Mesothelin-targeted CAR T cells based on antibody A101 or G8 were evaluated in a mouse model of mesothelioma. NSG mice were inoculated i.p. with H226 cells to establish tumors (FIG. 9A). Tumor-bearing mice were administered mock T cells or $20 \times 10^6$ CAR T cells via i.p. injection at day 13 after tumor cell inoculation. Tumor burden was monitored by bioluminescent imaging for 27 days (FIG. 9B). Quantitation of bioluminescence in mice is shown in FIG. 9C. A101 CAR T cells demonstrated antitumor activity and exhibited a trend toward eradication of H226 xenograft tumors.

Example 2: Identification of A101 and G8 Binding Epitopes on Human Mesothelin

This example describes further analysis of the epitopes of human mesothelin to which the A101 and G8 camel VHH antibodies bind.

Figure 10A:
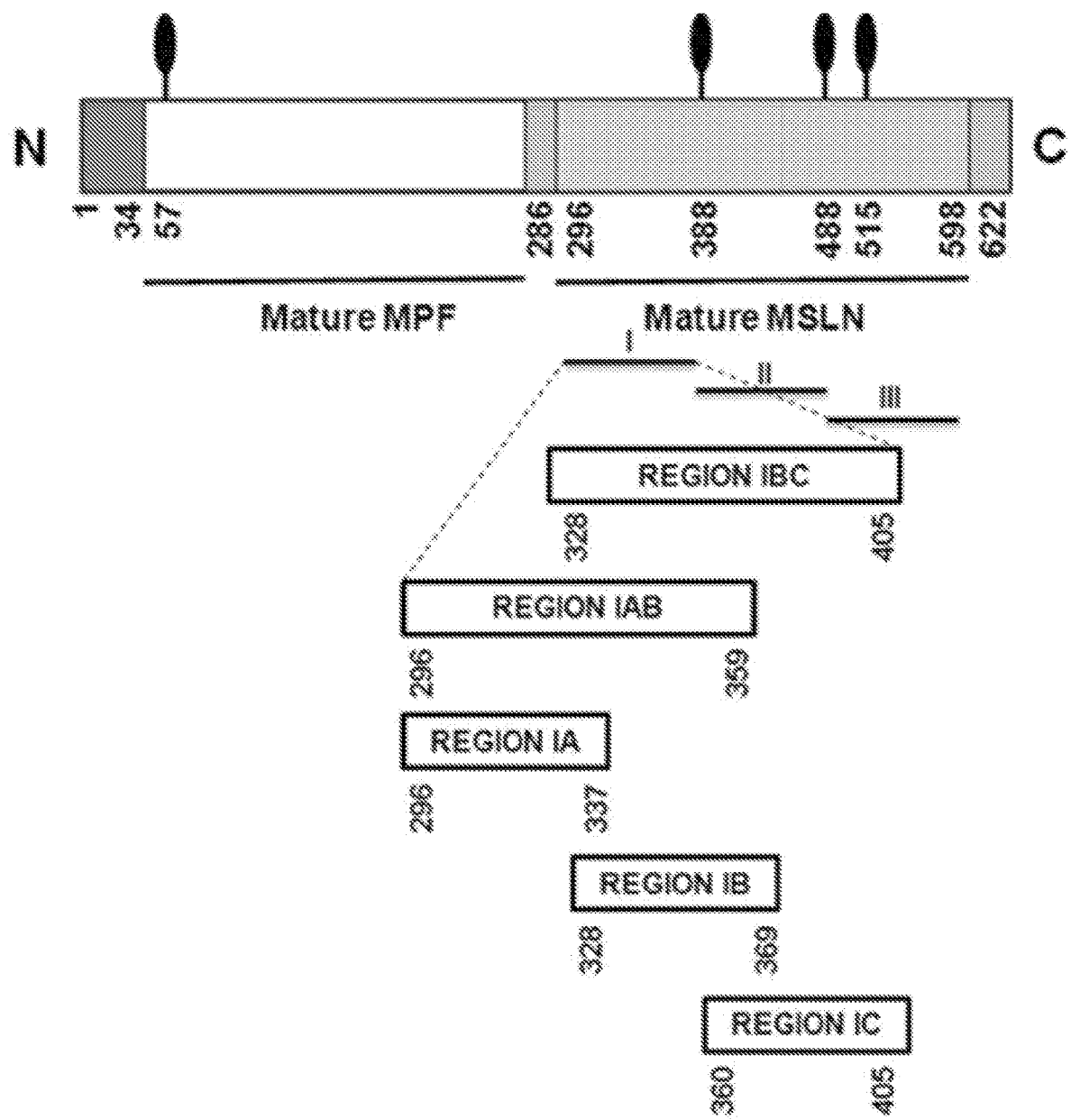
FIGS. 10A-10B: Binding epitopes on human mesothelin (SEQ ID NO: 12) for the A101 and G8 camel single domain antibodies.

Several fragments of human mesothelin were produced based on the human mesothelin amino acid sequence set forth as SEQ ID NO: 12 (FIG. 10A). The fragments included amino acid residues 296-390 (Region I), 391-486 (Region II), and 487-581 (Region III) of human mesothelin, as well as smaller fragments within Region I, specifically Region IAB (296-359), Region IBC (328-405), Region IA (296-337), Region IB (328-369), and Region IC (360-405). Region IAB (296-359) is the binding region for mesothelin's binding partner MUC16/CA125 (Kaneko et al., *J Biol Chem* 284(6): 3739-3749, 2009). Region IAB (269-359) mutants having either E321A, W321A or Y318A substitutions were also generated.

Figure 10B:
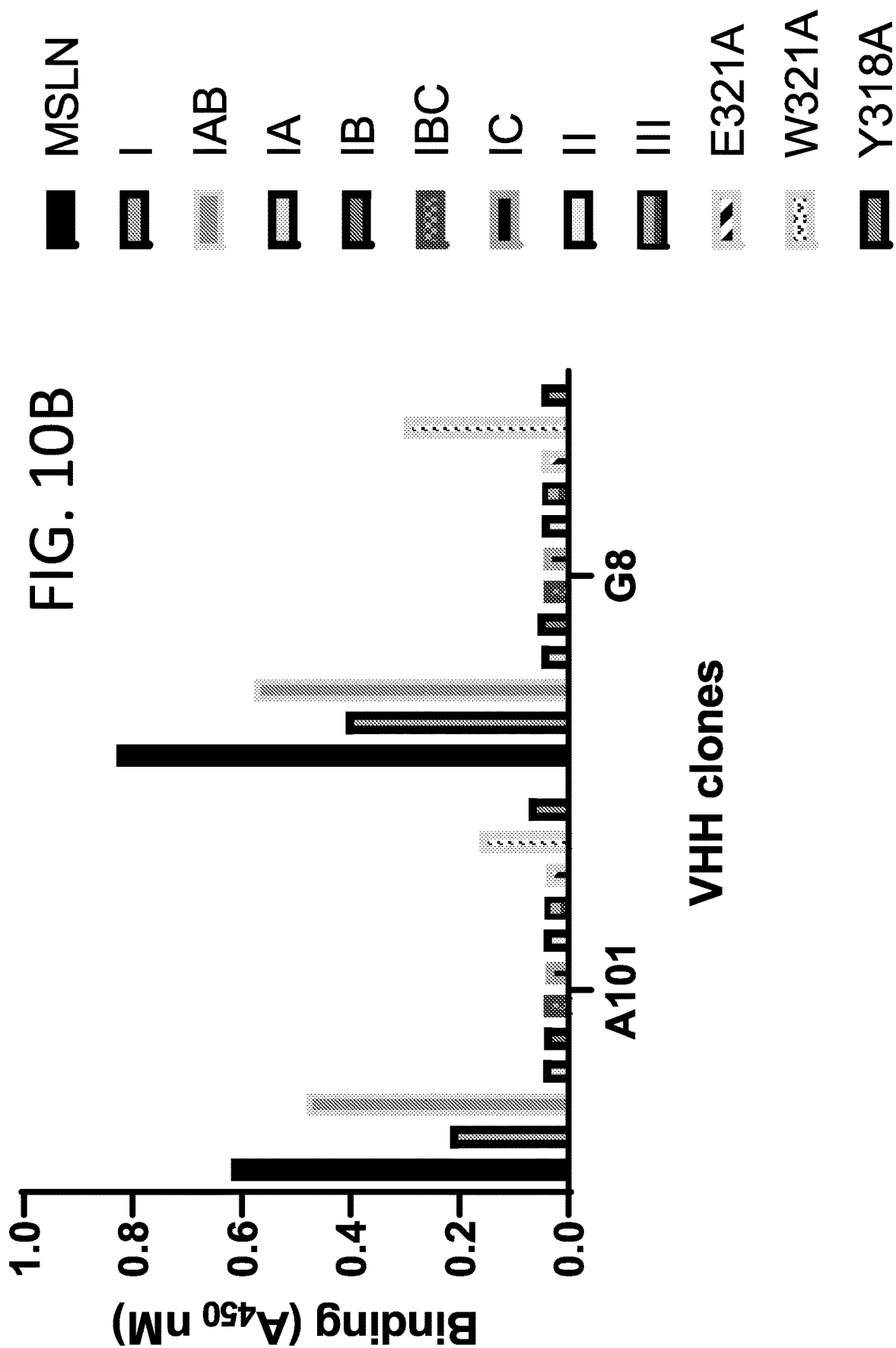

Binding of A101 and G8 to each mesothelin fragment was evaluated by ELISA (FIG. 10B). The results demonstrated that the A101 and G8 camel single domain antibodies mainly bind to the N-terminal Region I (296-390), including the IAB domain (64 residues, 296-359) which is the region required for MUC16 binding, indicating that the A101 and G8 antibodies could block MUC16/mesothelin interaction. In addition, when tyrosine residue 318 was mutated to alanine (Y318A), A101 and G8 binding was lost. Residue 318 is a critical site for MUC16 binding, thus MUC16 also does not bind the Y318A mutant. These results indicate that both single domain antibodies bind a ligand binding site for MUC16/CA125.

Example 3: In Vitro and In Vivo Activity of CAR T Cells Expressing A101 and G8

This example describes in vitro cell killing of mesothelin-positive cells and growth inhibition of mesothelin tumors in a xenograft animal model by A101 and G8 CAR T cells.

Figure 13A:
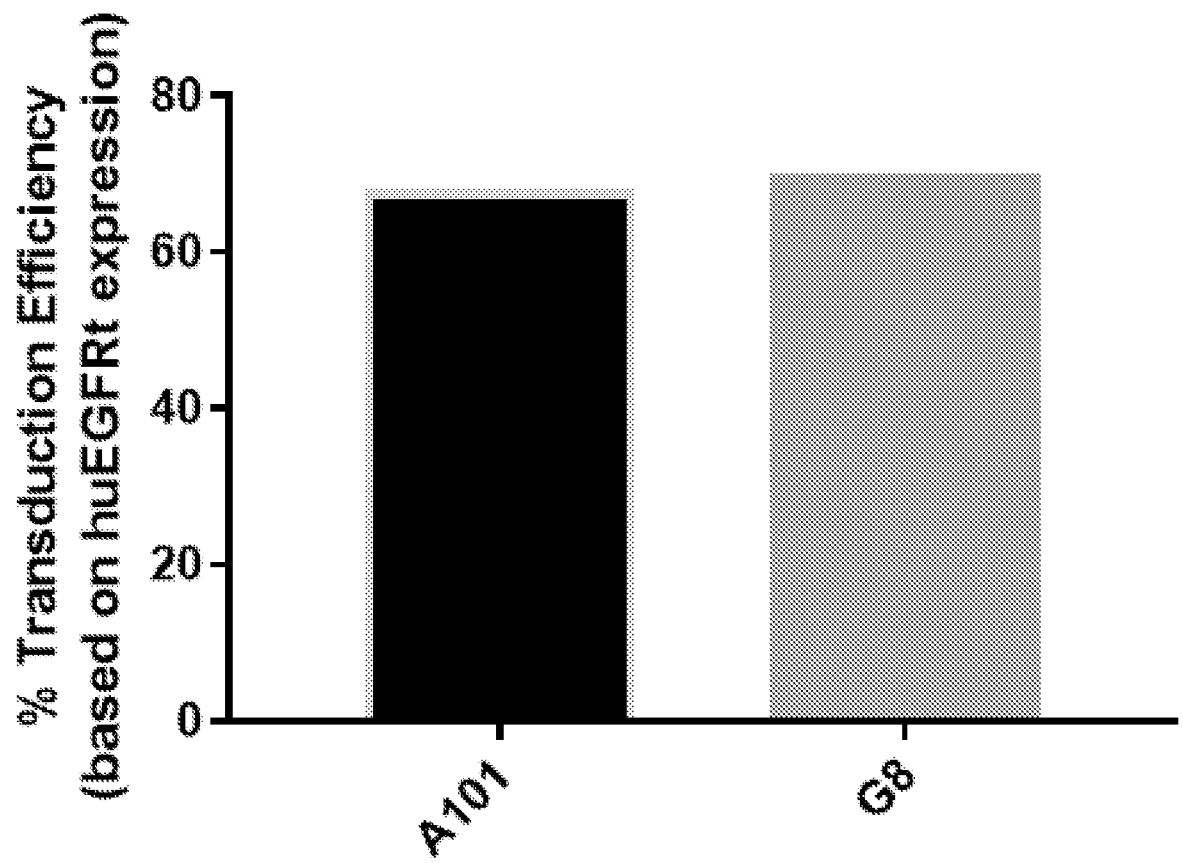
FIGS. 13A-13B: CAR T cells expressing the A101 and G8 antibodies kill mesothelin positive cell lines.
Figure 13B:
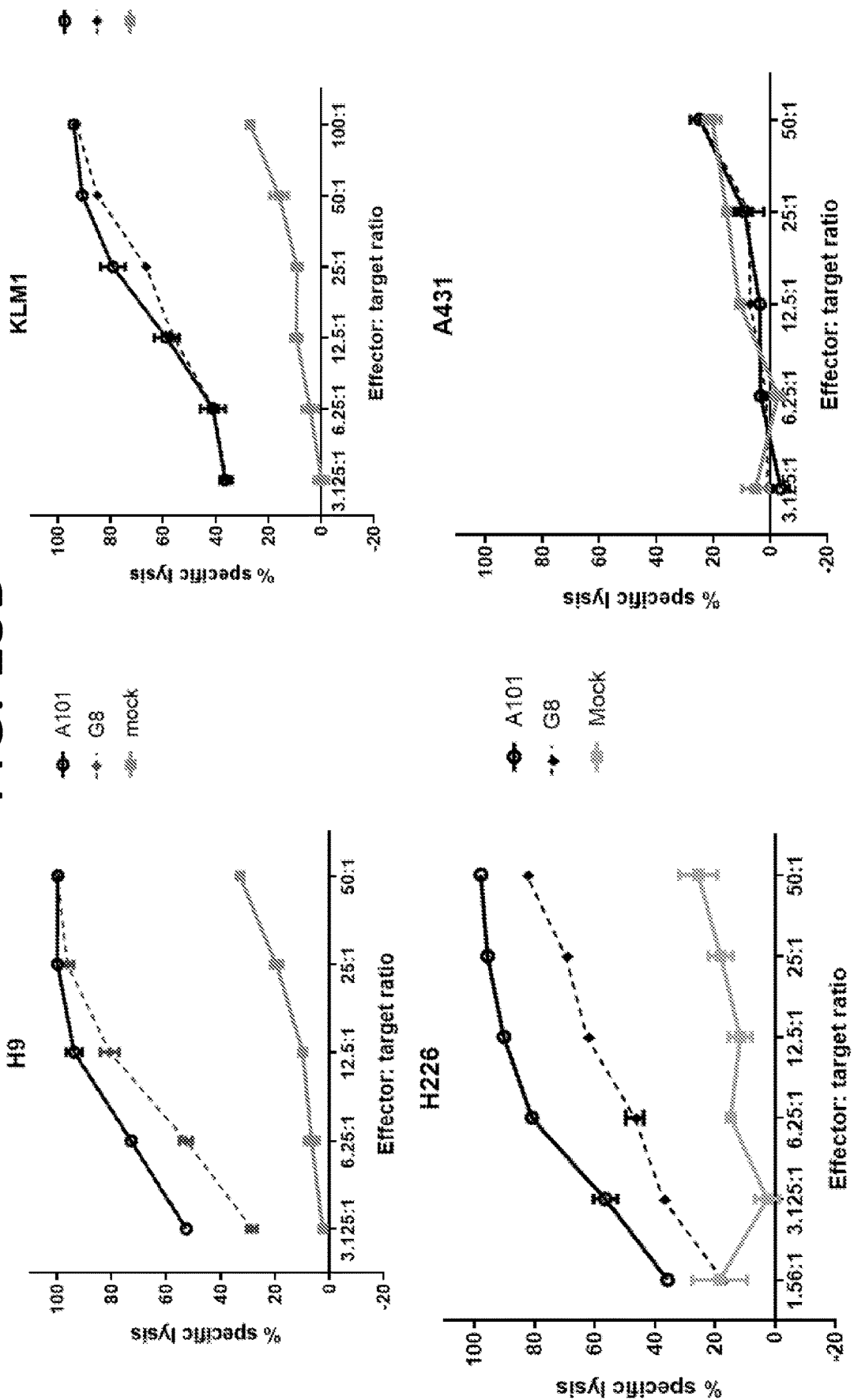

Generation of mesothelin-targeted CARs is described in Example 1. PBMCs from healthy donors were transduced with the A101 or G8 CAR T cells. Cetuximab was used to detect CARs on the cell surface. Transduction efficiency of the CAR T cells was greater than 60% (FIG. 13A). Next, the CAR T cells were evaluated in a CAR T cell killing assay using H9, a mesothelin over-expressing line; KLM1, a human pancreatic cancer line; H226, a human mesothelioma line; and A431, mesothelin-negative cells. Both A101 and G8 CAR T cells killed mesothelin-positive lines (H9, KLM1 and H226), but not mesothelin-negative cells (A431) (FIG. 13B). A101 CAR T cells showed better cytolytic activity than G8 CAR T cells in vitro.

Figure 14B:
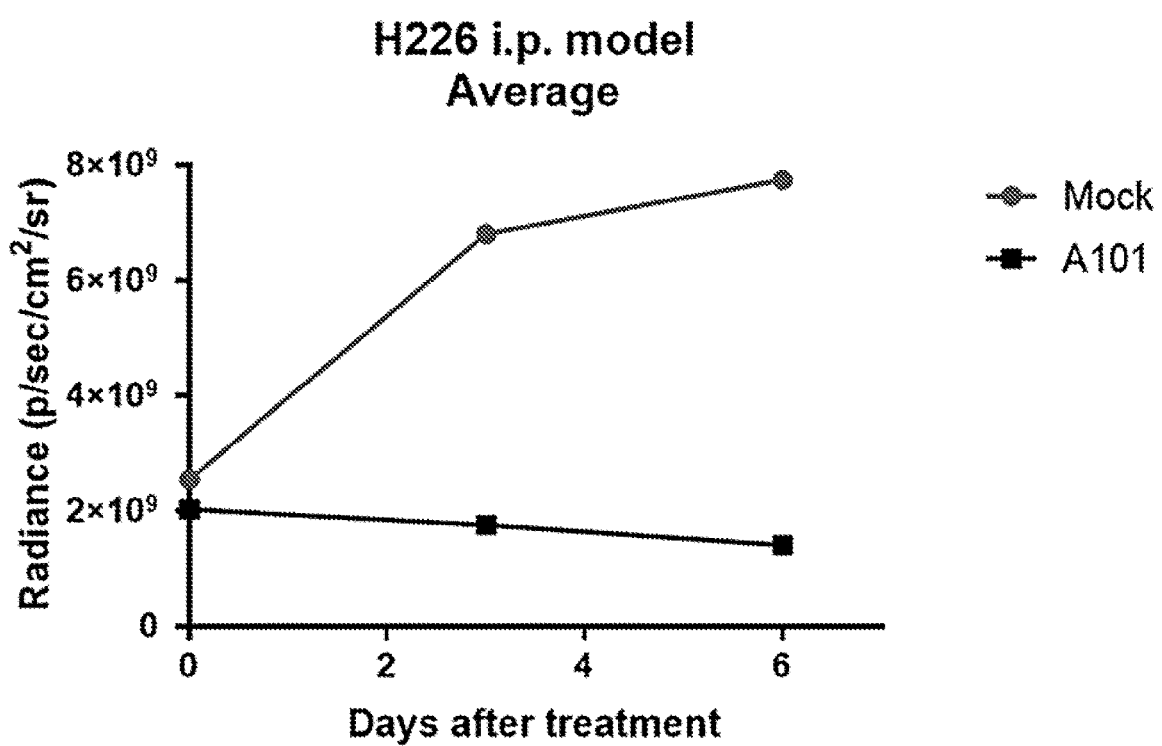

A101 CAR T cells were tested in mice bearing peritoneal human mesothelioma xenografts. Seven-week old female NSG mice were inoculated with 2M H226-luc cells. At day 3, animals were treated with either mock T cells or A101 CAR T cells (FIG. 14B, top). Tumor sizes were assessed by in vivo bioluminescence measurement using the IVIS Imaging System. Bioluminescence images of mock-treated and A101-treated mice are shown in FIG. 14A and radiance of mock-treated and A101-treated animals is shown in FIG. 14B (bottom). The results demonstrated that A101 CAR T cells effectively inhibited the growth of H226 xenograft tumors in mice.

In view of the many possible embodiments to which the principles of the disclosed subject matter may be applied, it should be recognized that the illustrated embodiments are only examples of the disclosure and should not be taken as limiting the scope of the disclosure. Rather, the scope of the disclosure is defined by the following claims.

The invention claimed is:

1. A single-domain monoclonal antibody that specifically binds mesothelin, wherein the monoclonal antibody comprises the complementarity determining region 1 (CDR1), CDR2 and CDR3 sequences of SEQ ID NO: 2 or SEQ ID NO: 4.

2. The monoclonal antibody of claim 1, wherein the CDR sequences are defined using the Kabat, IMGT or Paratome numbering schemes, or a combination of the Kabat, IMGT and Paratome numbering schemes.

3. The monoclonal antibody of claim 1, wherein:
the CDR1, CDR2 and CDR3 sequences of the monoclonal antibody respectively comprise residues 31-35, 50-66 and 99-10$^8$ of SEQ ID NO: 2;
the CDR1, CDR2 and CDR3 sequences of the monoclonal antibody respectively comprise residues 26-33, 51-58 and 97-10$^8$ of SEQ ID NO: 2; or
the CDR1, CDR2 and CDR3 sequences of the monoclonal antibody respectively comprise residues 27-35, 47-61 and 97-10$^8$ of SEQ ID NO: 2.

4. The monoclonal antibody of claim 1, wherein:
the CDR1, CDR2 and CDR3 sequences of the monoclonal antibody respectively comprise residues 31-35, 50-66 and 99-106 of SEQ ID NO: 4;
the CDR1, CDR2 and CDR3 sequences of the monoclonal antibody respectively comprise residues 26-33, 51-58 and 97-106 of SEQ ID NO: 4; or
the CDR1, CDR2 and CDR3 sequences of the monoclonal antibody respectively comprise residues 27-35, 47-60 and 98-106 of SEQ ID NO: 4.

5. The monoclonal antibody of claim 1, wherein:
the amino acid sequence of the monoclonal antibody is at least 95% identical to SEQ ID NO: 2 and comprises the CDR1, CDR2 and CDR3 sequences of SEQ ID NO: 2; or
the amino acid sequence of the monoclonal antibody is at least 95% identical to SEQ ID NO: 4 and comprises the CDR1, CDR2 and CDR3 sequences of SEQ ID NO: 4.

6. The monoclonal antibody of claim 1, wherein the amino acid sequence of the monoclonal antibody comprises or consists of SEQ ID NO: 2 or SEQ ID NO: 4.

7. The monoclonal antibody of claim 1, wherein the monoclonal antibody is a camel antibody, a humanized antibody, or a chimeric antibody.

8. A chimeric antigen receptor (CAR) comprising the monoclonal antibody of claim 1.

9. The CAR of claim 8, further comprising a hinge region, a transmembrane domain, a costimulatory signaling moiety, a signaling domain, or any combination thereof.

10. The CAR of claim 9, wherein
the hinge region comprises a CD8α hinge region;
the transmembrane domain comprises a CD8α transmembrane domain;
the costimulatory signaling moiety comprises a 4-1BB signaling moiety; and/or
the signaling domain comprises a CD3ξ signaling domain.

11. An isolated cell expressing the CAR of claim 8.

12. The isolated cell of claim 11, which is a cytotoxic T lymphocyte (CTL) or a natural killer (NK) cell.

13. An immunoconjugate comprising the monoclonal antibody of claim 1 and an effector molecule.

14. The immunoconjugate of claim 13, wherein the effector molecule is a toxin, a photon absorber, or a detectable label.

15. An antibody-drug conjugate (ADC) comprising a drug conjugated to the monoclonal antibody of claim 1.

16. The ADC of claim 15, wherein the drug is an anti-microtubule agent, an anti-mitotic agent and/or a cytotoxic agent.

17. A multi-specific antibody comprising the monoclonal antibody of claim 1 and at least one additional monoclonal antibody or antigen-binding fragment thereof.

18. The multi-specific antibody of claim 17, wherein the at least one additional monoclonal antibody or antigen binding fragment thereof specifically binds a component of the T cell receptor or a natural killer (NK) cell activating receptor.

19. An antibody-nanoparticle conjugate, comprising a nanoparticle conjugated to the monoclonal antibody of claim 1.

20. A fusion protein comprising the monoclonal antibody of claim 1 and a heterologous protein or peptide.

21. The fusion protein of claim 20, wherein the heterologous protein is an Fc protein.

22. An isolated nucleic acid molecule encoding the monoclonal antibody of claim 1.

23. The isolated nucleic acid molecule of claim 22, comprising the nucleotide sequence of SEQ ID NO: 1 or SEQ ID NO: 3, or a degenerate variant thereof.

24. The isolated nucleic acid molecule of claim 22, operably linked to a promoter.

25. A vector comprising the nucleic acid molecule of claim 22.

26. A nucleic acid molecule encoding a chimeric antigen receptor (CAR), comprising in the 5' to 3' direction:
- a nucleic acid encoding a first granulocyte-macrophage colony stimulating factor receptor signal sequence (GMCSFRss);
- a nucleic acid encoding the monoclonal antibody of claim 1;
- a nucleic acid encoding an extracellular hinge region;
- a nucleic acid encoding a transmembrane domain;
- a nucleic acid encoding an intracellular co-stimulatory domain;
- a nucleic acid encoding a intracellular signaling domain;
- a nucleic acid encoding a self-cleaving 2A peptide;
- a nucleic acid encoding a second GMCSFRss; and
- a nucleic acid encoding a truncated human epidermal growth factor receptor (huEGFRt).

27. The nucleic acid molecule of claim 26, further comprising a human elongation factor 1α (EF1α) promoter sequence 5' of the nucleic acid encoding the first GMCSFRss.

28. A vector comprising the nucleic acid molecule of claim 26.

29. An isolated cell comprising the claim 25.

30. A composition comprising a pharmaceutically acceptable carrier and the monoclonal antibody of claim 1.

31. A method of treating a mesothelin-positive cancer in a subject, comprising administering to the subject the monoclonal antibody of claim 1.

32. A method of inhibiting tumor growth or metastasis of a mesothelin-positive cancer in a subject, comprising administering to the subject the monoclonal antibody of claim 1.

33. The method of claim 31, wherein the mesothelin-positive cancer is a solid tumor.

34. The method of claim 31, wherein the mesothelin-positive cancer is a mesothelioma, prostate cancer, lung cancer, stomach cancer, squamous cell carcinoma, pancreatic cancer, cholangiocarcinoma, breast cancer or ovarian cancer.

35. A method of detecting expression of mesothelin in a sample, comprising:
- contacting the sample with the monoclonal antibody of claim 1; and
- detecting binding of the antibody to the sample, thereby detecting expression of mesothelin in the sample.

36. The method of claim 35, wherein the monoclonal antibody is directly labeled.

37. The method of claim 35, further comprising:
- contacting the monoclonal antibody with a detection antibody, and
- detecting the binding of the detection antibody to the monoclonal antibody, thereby detecting expression of mesothelin in the sample.

38. The method of claim 35, wherein the sample is obtained from a subject suspected of having a mesothelin-positive cancer.

39. The method of claim 35, wherein the sample is a tumor biopsy.

40. A method of diagnosing a subject as having a mesothelin-positive cancer, comprising:
- contacting a sample obtained from the subject with the monoclonal antibody of claim 1; and
- detecting binding of the antibody to the sample, thereby diagnosing the subject as having a mesothelin-positive cancer.

* * * * *

SEQUENCE LISTING

<160> NUMBER OF SEQ ID NOS: 12

<210> SEQ ID NO 1
<211> LENGTH: 358
<212> TYPE: DNA
<213> ORGANISM: Artificial Sequence
<220> FEATURE:
<223> OTHER INFORMATION: Synthetic polynucleotide (A101)

<400> SEQUENCE: 1

```
caggtgcagc tggtggagtc tgggggcggc acggtgcagg ctggagggtc gctgaaactc      60
gcctgcgcag cctctggatt acccagaacg tacaatgtca tgggctggtt ccgccaggcc     120
ccagggaagg agcgcgaggg ggtcgcaata atttatacta cgactggagc aacatactat     180
cgcgactccg tcaagggccg ggccaccatc tcccaagaca acgccaagaa gtcggtgtct     240
ctccaaatga acagcctgag gcctgaggac acggccatct attactgtgt ggctaggcaa     300
cccaatagtg gtccctggga gtattggggc caggggaccc aggtcaccgt ctcctcaa      358
```

<210> SEQ ID NO 2
<211> LENGTH: 119
<212> TYPE: PRT
<213> ORGANISM: Artificial Sequence
<220> FEATURE:
<223> OTHER INFORMATION: Synthetic polypeptide (A101)

<400> SEQUENCE: 2

```
Gln Val Gln Leu Val Glu Ser Gly Gly Gly Thr Val Gln Ala Gly Gly
  1               5                  10                  15

Ser Leu Lys Leu Ala Cys Ala Ala Ser Gly Leu Pro Arg Thr Tyr Asn
             20                  25                  30

Val Met Gly Trp Phe Arg Gln Ala Pro Gly Lys Glu Arg Glu Gly Val
         35                  40                  45

Ala Ile Ile Tyr Thr Thr Thr Gly Ala Thr Tyr Tyr Arg Asp Ser Val
     50                  55                  60

Lys Gly Arg Ala Thr Ile Ser Gln Asp Asn Ala Lys Lys Ser Val Ser
 65                  70                  75                  80

Leu Gln Met Asn Ser Leu Arg Pro Glu Asp Thr Ala Ile Tyr Tyr Cys
                 85                  90                  95

Val Ala Arg Gln Pro Asn Ser Gly Pro Trp Glu Tyr Trp Gly Gln Gly
            100                 105                 110

Thr Gln Val Thr Val Ser Ser
        115
```

<210> SEQ ID NO 3
<211> LENGTH: 351
<212> TYPE: DNA
<213> ORGANISM: Artificial Sequence
<220> FEATURE:
<223> OTHER INFORMATION: Synthetic polynucleotide (G8)

<400> SEQUENCE: 3

```
caggtaaagc tggaggagtc tgggggaggc tcggtgcagg ctggagggtc tctgagactc      60
tcctgtacaa cttctggata caccaacagt tacaagtgga tgggctggtt ccgccaggct     120
ccaggacaag agcgcgaggg ggtcgcagtt atttacaccg gtaatgatag acatactat      180
agtgactccg tgaagggccg attcaccatc tcccgagaca acgccaagaa tatgatctat     240
ctggacatga gcgcgcctgag acctgaggac agcgctgtgt acgagtgtgc catcggacat     300
gatggcgcat ggcgttactg gggccaggga acgcaggtca ccgtctcctc a              351
```

<210> SEQ ID NO 4
<211> LENGTH: 117
<212> TYPE: PRT
<213> ORGANISM: Artificial Sequence
<220> FEATURE:
<223> OTHER INFORMATION: Synthetic polypeptide (G8)

<400> SEQUENCE: 4

Gln Val Lys Leu Glu Glu Ser Gly Gly Ser Val Gln Ala Gly Gly
1               5                   10                  15

Ser Leu Arg Leu Ser Cys Thr Thr Ser Gly Tyr Thr Asn Ser Tyr Lys
                20                  25                  30

Trp Met Gly Trp Phe Arg Gln Ala Pro Gly Gln Glu Arg Glu Gly Val
            35                  40                  45

Ala Val Ile Tyr Thr Gly Asn Asp Arg Thr Tyr Tyr Ser Asp Ser Val
        50                  55                  60

Lys Gly Arg Phe Thr Ile Ser Arg Asp Asn Ala Lys Asn Met Ile Tyr
65                  70                  75                  80

Leu Asp Met Thr Arg Leu Arg Pro Glu Asp Ser Ala Val Tyr Glu Cys
                85                  90                  95

Ala Ile Gly His Asp Gly Ala Trp Arg Tyr Trp Gly Gln Gly Thr Gln
            100                 105                 110

Val Thr Val Ser Ser
        115

<210> SEQ ID NO 5
<211> LENGTH: 22
<212> TYPE: PRT
<213> ORGANISM: Homo sapiens

<400> SEQUENCE: 5

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 6
<211> LENGTH: 45
<212> TYPE: PRT
<213> ORGANISM: Homo sapiens

<400> SEQUENCE: 6

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
            35                  40                  45

<210> SEQ ID NO 7
<211> LENGTH: 21
<212> TYPE: PRT
<213> ORGANISM: Homo sapiens

<400> SEQUENCE: 7

Ile Tyr Ile Trp Ala Pro Leu Ala Gly Thr Cys Gly Val Leu Leu Leu
1               5                   10                  15

Ser Leu Val Ile Thr
        20

<210> SEQ ID NO 8
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 8

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 9
<211> LENGTH: 112
<212> TYPE: PRT
<213> ORGANISM: Homo sapiens

<400> SEQUENCE: 9

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 10
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 10

Glu Gly Arg Gly Ser Leu Leu Thr Cys Gly Asp Val Glu Glu Asn Pro
1               5                   10                  15

Gly Pro

<210> SEQ ID NO 11
<211> LENGTH: 335
<212> TYPE: PRT
<213> ORGANISM: Homo sapiens

<400> SEQUENCE: 11

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe

```
            35                  40                  45
Thr His Thr Pro Pro Leu Asp Pro Gln Glu Leu Asp Ile Leu Lys Thr
 50                  55                  60
Val Lys Glu Ile Thr Gly Phe Leu Leu Ile Gln Ala Trp Pro Glu Asn
 65                  70                  75                  80
Arg Thr Asp Leu His Ala Phe Glu Asn Leu Glu Ile Ile Arg Gly Arg
                     85                  90                  95
Thr Lys Gln His Gly Gln Phe Ser Leu Ala Val Val Ser Leu Asn Ile
                    100                 105                 110
Thr Ser Leu Gly Leu Arg Ser Leu Lys Glu Ile Ser Asp Gly Asp Val
                    115                 120                 125
Ile Ile Ser Gly Asn Lys Asn Leu Cys Tyr Ala Asn Thr Ile Asn Trp
    130                 135                 140
Lys Lys Leu Phe Gly Thr Ser Gly Gln Lys Thr Lys Ile Ile Ser Asn
145                 150                 155                 160
Arg Gly Glu Asn Ser Cys Lys Ala Thr Gly Gln Val Cys His Ala Leu
                    165                 170                 175
Cys Ser Pro Glu Gly Cys Trp Gly Pro Glu Pro Arg Asp Cys Val Ser
                180                 185                 190
Cys Arg Asn Val Ser Arg Gly Arg Glu Cys Val Asp Lys Cys Asn Leu
            195                 200                 205
Leu Glu Gly Glu Pro Arg Glu Phe Val Glu Asn Ser Glu Cys Ile Gln
        210                 215                 220
Cys His Pro Glu Cys Leu Pro Gln Ala Met Asn Ile Thr Cys Thr Gly
225                 230                 235                 240
Arg Gly Pro Asp Asn Cys Ile Gln Cys Ala His Tyr Ile Asp Gly Pro
                    245                 250                 255
His Cys Val Lys Thr Cys Pro Ala Gly Val Met Gly Glu Asn Asn Thr
                260                 265                 270
Leu Val Trp Lys Tyr Ala Asp Ala Gly His Val Cys His Leu Cys His
            275                 280                 285
Pro Asn Cys Thr Tyr Gly Cys Thr Gly Pro Gly Leu Glu Gly Cys Pro
        290                 295                 300
Thr Asn Gly Pro Lys Ile Pro Ser Ile Ala Thr Gly Met Val Gly Ala
305                 310                 315                 320
Leu Leu Leu Leu Leu Val Val Ala Leu Gly Ile Gly Leu Phe Met
                    325                 330                 335

<210> SEQ ID NO 12
<211> LENGTH: 622
<212> TYPE: PRT
<213> ORGANISM: Homo sapiens

<400> SEQUENCE: 12

Met Ala Leu Pro Thr Ala Arg Pro Leu Leu Gly Ser Cys Gly Thr Pro
1               5                  10                  15
Ala Leu Gly Ser Leu Leu Phe Leu Leu Phe Ser Leu Gly Trp Val Gln
                    20                  25                  30
Pro Ser Arg Thr Leu Ala Gly Glu Thr Gly Gln Glu Ala Ala Pro Leu
                35                  40                  45
Asp Gly Val Leu Ala Asn Pro Pro Asn Ile Ser Ser Leu Ser Pro Arg
            50                  55                  60
Gln Leu Leu Gly Phe Pro Cys Ala Glu Val Ser Gly Leu Ser Thr Glu
65                  70                  75                  80
```

```
Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Phe Leu Asn Pro
        115                 120                 125

Asp Ala Phe Ser Gly Pro Gln Ala Cys Thr Arg Phe Phe Ser Arg Ile
130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Pro Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
```

-continued

```
                500                 505                 510
Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
        530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
        580                 585                 590

Met Gln Glu Ala Leu Ser Gly Thr Pro Cys Leu Leu Gly Pro Gly Pro
        595                 600                 605

Val Leu Thr Val Leu Ala Leu Leu Leu Ala Ser Thr Leu Ala
        610                 615                 620
```